(12) United States Patent
Dunn et al.

(10) Patent No.: US 12,409,292 B2
(45) Date of Patent: Sep. 9, 2025

(54) ULTRASONIC WELDING OF FABRICS FOR SLEEP APNEA TREATMENT

(71) Applicant: ResMed Pty Ltd, Bella Vista (AU)

(72) Inventors: Jessica Lea Dunn, Scotts Head (AU); Grant Milton Ovzinsky, Sydney (AU); Anthony Paul Barbara, Smithfield (AU); Kirrily Michele Haskard, Annandale (AU); Justin John Formica, Sydney (AU); Michael Charles La Guzza, Carlingford (AU)

(73) Assignee: ResMed Pty Ltd (AU)

(*) Notice: Subject to any disclaimer, the term of this patent is extended or adjusted under 35 U.S.C. 154(b) by 195 days.

(21) Appl. No.: 17/879,868

(22) Filed: Aug. 3, 2022

(65) Prior Publication Data
US 2022/0370749 A1 Nov. 24, 2022

Related U.S. Application Data

(63) Continuation of application No. 16/243,575, filed on Jan. 9, 2019, now Pat. No. 11,458,271, which is a
(Continued)

(51) Int. Cl.
*A61M 16/06* (2006.01)
*B29C 65/00* (2006.01)
(Continued)

(52) U.S. Cl.
CPC ......... *A61M 16/0683* (2013.01); *B29C 65/08* (2013.01); *B29C 65/7443* (2013.01);
(Continued)

(58) Field of Classification Search
CPC ....... A61M 16/0683; A62B 18/08; A62B 9/00
See application file for complete search history.

(56) References Cited

U.S. PATENT DOCUMENTS

| 2,643,380 A | 6/1953 | Blair |
|---|---|---|
| 3,280,406 A | 10/1966 | Immel |

(Continued)

FOREIGN PATENT DOCUMENTS

| CN | 1990215 A | 7/2007 |
|---|---|---|
| CN | 100508805 C | 7/2009 |

(Continued)

OTHER PUBLICATIONS

CN Office Action issued Apr. 13, 2020 for CN Patent Application No. 2018100325834.
(Continued)

*Primary Examiner* — Margaret M Luarca
(74) *Attorney, Agent, or Firm* — Botos Churchill IP Law LLP

(57) ABSTRACT

A respiratory apparatus may employ ultrasonic welds. The ultrasonic welding may be used to join a variety of headgear, mask and accessory components. This process may enhance comfort, fit and/or performance of the joined components and/or overall mask assembly. A component may be a single layer component such as a textile or fabric, or a composite or multiple layer component such as fabric and foam composites, or outer fabric layers and inner spacer fabrics. Further, a component may be a strap, some other headgear component, a mask component, an accessory component or the like.

10 Claims, 21 Drawing Sheets

Related U.S. Application Data continuation of application No. 14/240,167, filed as application No. PCT/AU2012/000981 on Aug. 22, 2012, now Pat. No. 10,207,072.

(60) Provisional application No. 61/526,042, filed on Aug. 22, 2011.

(51) Int. Cl.
| | | |
|---|---|---|
| *B29C 65/08* | (2006.01) | |
| *B29C 65/74* | (2006.01) | |
| *B29C 65/48* | (2006.01) | |
| *B29C 65/50* | (2006.01) | |
| *B29C 65/62* | (2006.01) | |
| *B29L 31/48* | (2006.01) | |

(52) U.S. Cl.
CPC .......... *B29C 66/1142* (2013.01); *B29C 66/14* (2013.01); *B29C 66/43* (2013.01); *B29C 66/4322* (2013.01); *B29C 66/4344* (2013.01); *B29C 66/43441* (2013.01); *B29C 66/436* (2013.01); *B29C 66/729* (2013.01); *B29C 66/73521* (2013.01); *A61M 16/0633* (2014.02); *A61M 2207/00* (2013.01); *B29C 65/48* (2013.01); *B29C 65/4815* (2013.01); *B29C 65/5042* (2013.01); *B29C 65/62* (2013.01); *B29C 66/71* (2013.01); *B29C 66/723* (2013.01); *B29C 66/727* (2013.01); *B29L 2031/4835* (2013.01); *F04C 2270/0421* (2013.01)

(56) References Cited

U.S. PATENT DOCUMENTS

| | | | |
|---|---|---|---|
| 3,819,437 A | 6/1974 | Paine | |
| 3,874,968 A | 4/1975 | Robinson | |
| 4,575,874 A * | 3/1986 | Johnson | A41F 15/007 2/460 |
| 5,552,005 A | 9/1996 | Mammino | |
| 5,558,556 A * | 9/1996 | Froehlich | A41F 15/007 2/268 |
| 5,566,871 A * | 10/1996 | Weintraub | A45F 3/12 224/264 |
| 6,422,238 B1 | 7/2002 | Lithgow | |
| 6,625,820 B1 | 9/2003 | Lampe | |
| 6,772,760 B2 | 8/2004 | Frater et al. | |
| 7,878,200 B2 | 2/2011 | Zollinger et al. | |
| 8,136,525 B2 | 3/2012 | Lubke et al. | |
| 9,072,855 B2 | 7/2015 | Mcauley | |
| 2007/0186931 A1 | 8/2007 | Zollinger et al. | |
| 2007/0261212 A1 | 11/2007 | Russell | |
| 2008/0034463 A1 | 2/2008 | Ekelund et al. | |
| 2008/0216629 A1 | 9/2008 | Herko | |
| 2008/0295947 A1 | 12/2008 | Bourbeau et al. | |
| 2009/0211583 A1 | 8/2009 | Carroll et al. | |
| 2010/0258132 A1 | 10/2010 | Moore | |
| 2010/0258136 A1 | 10/2010 | Doherty et al. | |
| 2011/0072553 A1 | 3/2011 | Ho | |
| 2011/0197341 A1 | 8/2011 | Formica et al. | |

FOREIGN PATENT DOCUMENTS

| | | |
|---|---|---|
| EP | 2130563 A1 | 12/2009 |
| EP | 3718586 A1 | 10/2020 |
| GB | 2482990 A | 2/2012 |
| KR | 100615863 B1 | 8/2006 |
| WO | 2005076874 A2 | 8/2005 |
| WO | 2005099801 A1 | 10/2005 |
| WO | 2006130903 A1 | 12/2006 |
| WO | 2009059353 A1 | 5/2009 |
| WO | 2010066004 A1 | 6/2010 |
| WO | 2011014931 A1 | 2/2011 |
| WO | 2011022779 A1 | 3/2011 |
| WO | 2012027792 A1 | 3/2012 |
| WO | 2013026091 A1 | 2/2013 |

OTHER PUBLICATIONS

EP Communication dated Feb. 25, 2020 for EP Application No. 17 204 178.2-1122.

Extended European Search Report for Application No. EP12825926 dated Jan. 29, 2015.

International Search Report for Application No. PCT/AU2012/000981 dated Dec. 14, 2012.

PCT Written Opinion for Application No. PCT/AU2012/000981 dated Dec. 14, 2012.

European Search Report from corresponding EP Application No. 22 166 679.5 dated Aug. 11, 2022.

Office Action issued in corresponding European Patent Application No. 22166679.5, mailed May 7, 2024, 6 pages.

* cited by examiner

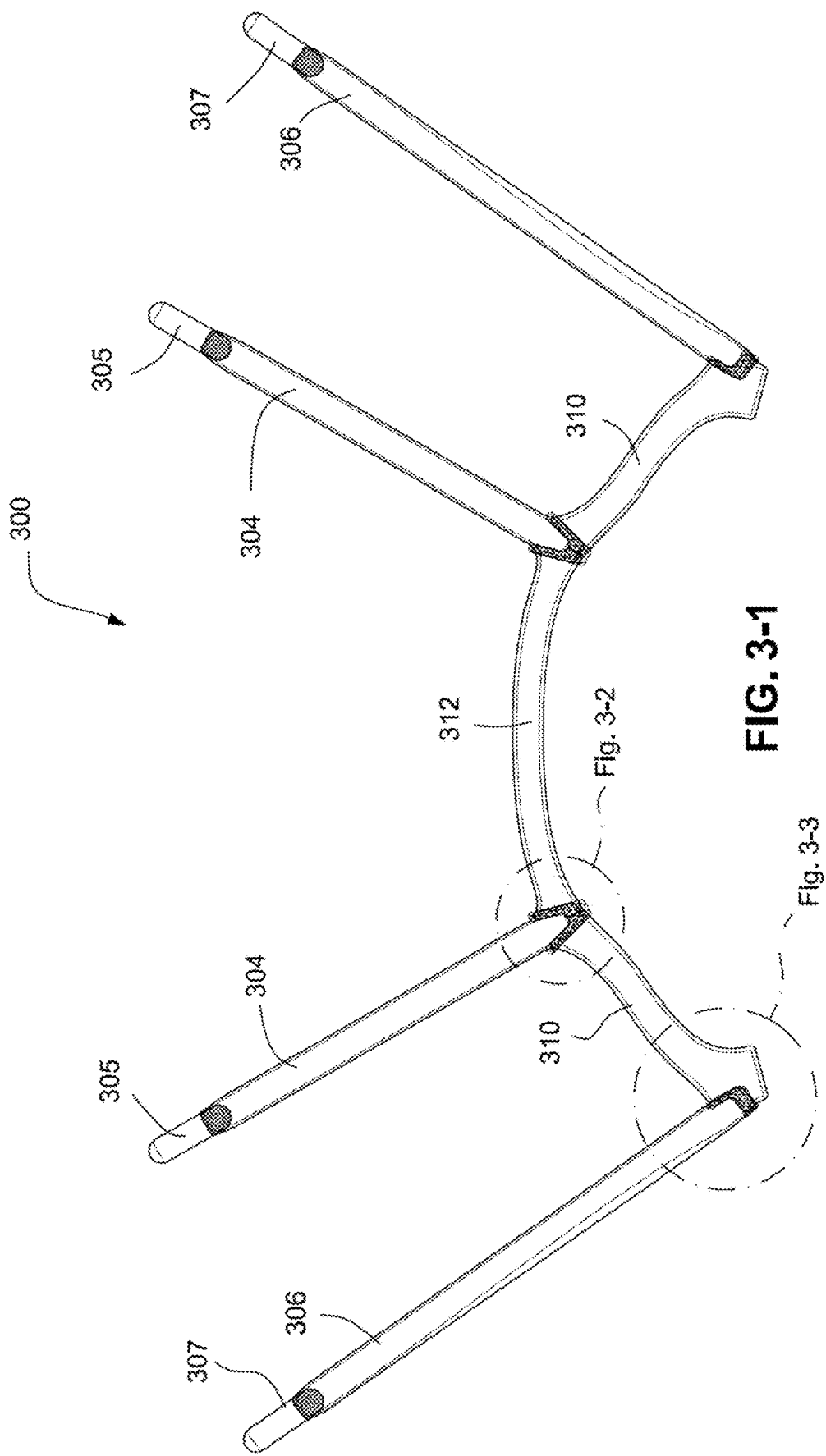

ULTRASONIC WELDING OF FABRICS FOR SLEEP APNEA TREATMENT

CROSS-REFERENCE RELATED TO APPLICATION

The present application is a continuation of U.S. patent application Ser. No. 16/243,575, filed Jan. 9, 2019, which is a continuation of U.S. patent application Ser. No. 14/240,167, filed Feb. 21, 2014, now U.S. Pat. No. 10,207,072, which is a national phase entry under 35 U.S.C. § 371 of International Application No. PCT/AU2012/000981, filed Aug. 22, 2012, which claims priority from U.S. Provisional Patent Application No. 61/526,042, filed Aug. 22, 2011, all of which are hereby incorporated herein by reference.

FIELD OF TECHNOLOGY

The present technology relates to headgear and masks, and a method of constructing them. Such masks may be suitable for use in respiratory treatment, e.g., sleep disordered breathing with continuous positive airway pressure or non-invasive positive pressure ventilation.

BACKGROUND OF TECHNOLOGY

Masks used for treatment of Sleep Disordered Breathing (SDB) such as Obstructive Sleep Apnea (OSA) are typically held on a patient's head by headgear. Headgear typically includes one or more headgear straps that are adapted to engage with the mask and hold the mask in position on the patient's face.

U.S. Pat. No. 6,422,238 to Lithgow discloses headgear for securing a respiratory mask having a quick release arrangement to a patient. U.S. Pat. No. 6,772,760 to Frater et al. discloses a mask system for delivering air to a user including a suspension mechanism to allow relative movement between a face-contacting cushion a mask shell. U.S. Pat. No. 8,136,525 to Lubke et al. discloses a mask system for use between a patient and a device to deliver a breathable gas to the patient, the system having a mouth cushion, a pair of nasal prongs, an elbow, and a headgear assembly. The headgear assembly provides a substantially round crown strap that cups the parietal bone and occipital bone of the patient's head during use. U.S. Pat. No. 7,878,200 to Zollinger et al. discloses a headgear for securing a patient airway interface device to a patient's head, and in particular an infant patient. The headgear includes a central body, first and second forehead straps, and first and second lower straps.

Headgear and masks should be comfortable so that a patient can wear the mask at night while they sleep. There is a continuous need in the art for headgear and masks that are comfortable, fit a wide range of patients, are easily manufactured, and are inexpensive.

SUMMARY OF TECHNOLOGY

A first aspect of the disclosed technology relates to a method of making headgear comprising ultrasonically welding components in a manner that enhances comfort, fit and/or performance.

Another aspect of the disclosed technology relates to a method of making headgear comprising ultrasonically welding at least first and second headgear components to create a flush joint.

Another aspect of the disclosed technology relates to a method of making headgear comprising ultrasonically welding at least first and second headgear components in a manner that locates ultrasonic welding joints to create a flush joint. The flush joint may be adapted to connect the first and second headgear components without substantially increasing the thickness of the headgear i.e. the thickness of the headgear is the greater of the thicknesses of the first and second headgear components and not the sum of the thicknesses of the first and second headgear components.

Another aspect of the disclosed technology relates to a method of making headgear comprising ultrasonically welding at least first and second headgear components in a manner that locates ultrasonic welding joints to create a flush joint. The flush joint may be reinforced. The overall thickness of the joint may be equal to the thickness of the greater one of the first and second components, plus the thickness of the reinforcing.

Another aspect of the disclosed technology relates to a method of making headgear comprising joining at least first and second headgear components to create a flush joint. The method of joining the at least first and second headgear components may include heat embossing, or using lasers (such as $CO_2$ lasers), hot air, or a heated plate or knife.

Another aspect of the disclosed technology relates to a method of making headgear comprising ultrasonically welding at least first and second headgear components in a manner that locates ultrasonic welding joints to allow or disallow flexibility in at least one portion of the combined components.

Another aspect of the disclosed technology relates to a method of making headgear comprising ultrasonically welding a substantially flat first headgear component to a curved second headgear component, wherein the curved second headgear component is attached at an edge portion of the flat first headgear component to provide a rounded surface at the area of patient contact to increase comfort for the patient.

Another aspect of the present technology relates to a method of making headgear comprising ultrasonically welding a first fabric having a first stiffness to a second fabric having a second stiffness, wherein the first fabric is wider than the second fabric and the first stiffness is greater than the second stiffness.

Another aspect of the disclosed technology relates to a method of making headgear comprising ultrasonically welding together a strap and a fastening member such that a portion of the strap is removed and the fastening member is nested within the portion of the strap in a recessed manner.

Another aspect of the disclosed technology relates to a method of making headgear comprising ultrasonically welding together a more rigid, less flexible member and a more flexible, less rigid member in an alternating manner to allow or disallow flexibility in at least one portion of the headgear.

Another aspect of the disclosed technology relates to a method of making headgear for use in holding a respiratory mask in position on a patient's face. The method comprises forming at least first and second headgear components each including at least a fabric material, overlapping the at least first and second headgear components in an ultrasonic welding tool, removing an overlapping portion from at least one of the first and second headgear components, and in the 'cut and seal' process described, ultrasonically welding together the at least first and second headgear components to form an ultrasonic welding joint, thereby forming at least one headgear section. The resulting ultrasonic 'butt' or 'flush' joint may then be reinforced by means of any one or more of stitching, tacking, overmoulding with a polymer, spot welding, applying a thin fabric with an adhesive backing, applying hot-melt seam tape, and/or other method of reinforcement.

Another aspect of the disclosed technology relates to a method of making a comfort pad for use with headgear in holding a respiratory mask in position on a patient's face. The method comprises ultrasonically welding a padded member to a first substantially flat member thereby forming a first ultrasonic welding joint, wherein the padded member is arranged to provide a cushion between the patient and the headgear, and the first flat member is arranged to overwrap the headgear to position the padded member on the patient's face.

Another aspect of the disclosed technology relates to a method of forming a mask assembly for use in treating a patient for sleep disordered breathing. The method comprises ultrasonically welding a first component to a second component thereby forming at least a first mask section, wherein first mask section at least partially forms a cavity that delivers pressurized air to the patient. The resulting ultrasonic 'butt' or 'flush' joint may then be reinforced by means of stitching, tacking, overmoulding with a polymer, spot welding, applying a thin fabric with an adhesive backing, applying hot-melt seam tape, and/or other method of reinforcement.

Another aspect of the disclosed technology relates to a mask assembly for use in treating a patient for sleep disordered breathing. The mask assembly comprises a first component, a second component, and an ultrasonic welding joint which may be overlapped, or flush joined, or reinforced, interconnecting the first component and the second component by way of creating an overlap or a flush weld thereby forming at least a first mask section, wherein the first mask section at least partially forms a cavity that delivers pressurized air to the patient.

Another aspect of the disclosed technology relates to a headgear for use in supporting a respiratory mask in position on a patient's face for positive pressure treatment of the patient. The headgear comprises a first headgear component and a second headgear component, wherein the first and second headgear components include at least a fabric material which may be laminated to a membrane or foam layer, or have multiple layers, or comprised of a three-dimensional spacer fabric construction, or could be of a knitted, woven or non-woven construction. An ultrasonic welding joint interconnects the first headgear component and the second headgear component thereby forming at least a first headgear section, wherein a space is formed between the first and second headgear components.

Another aspect of the disclosed technology relates to a method of making headgear for use in holding a respiratory mask in position on a patient's face. The method comprises ultrasonically welding a first headgear component to a second headgear component thereby forming at least a first headgear section having a space situated between the first headgear component and the second headgear component, the first and second headgear components including at least a fabric material.

Another aspect of the disclosed technology relates to a headgear for use in supporting a respiratory mask in position on a patient's face for positive pressure treatment of the patient. The headgear comprises a first headgear component formed of a first fabric and a second headgear component formed of a second fabric, wherein the second fabric is softer than the first fabric. An ultrasonic welding joint interconnects the first headgear component and the second headgear component thereby forming at least a first headgear section, wherein the first and second headgear components are connected to one another such that the second headgear component covers a portion of the first headgear component.

Another aspect of the disclosed technology relates to a method of making headgear for use in holding a respiratory mask in position on a patient's face. The method comprises nesting first headgear components in at least one sheet of material, nesting second headgear components in the at least one sheet of material, cutting the first and second headgear components from the at least one sheet of material, and ultrasonically welding the first headgear components and the second headgear components to form at least one headgear.

Another aspect of the disclosed technology relates to headgear for use in supporting a respiratory mask in position on a patient's face for positive pressure treatment of the patient. The headgear comprises a first strap having a first vector, a second strap having a second vector different from the first vector, and an ultrasonic welding joint interconnecting the first strap and the second strap thereby forming at least a first headgear section. To prevent the joint from tearing or delaminating, it may be reinforced by means of stitching, tacking, overmoulding with a polymer, spot welding, applying a thin fabric with an adhesive backing, applying hot-melt seam tape, or other method of reinforcement.

Another aspect of the disclosed technology relates to headgear for use in supporting a respiratory mask in position on a patient's face for positive pressure treatment of the patient. The headgear comprises a substantially flat member including at least a fabric material and a curved member joined to the flat member by ultrasonic welding thereby forming a seamless joint, wherein the curved member is attached at an edge portion of the flat member to provide a rounded surface to increase comfort for the patient.

While the above aspects are described in relation to methods or headgear being made in part by ultrasonic welding, it is noted that such ultrasonic welding is not necessary, as alternative joining techniques may be used.

Other aspects, features, and advantages of this technology will become apparent from the following detailed description when taken in conjunction with the accompanying drawings, which are a part of this disclosure and which illustrate, by way of example, principles of this technology.

BRIEF DESCRIPTION OF THE DRAWINGS

The accompanying drawings facilitate an understanding of the various embodiments of this technology. In such drawings:

FIG. 2-1 is a perspective view of headgear according to an example of the disclosed technology;

FIG. 2-2 is a perspective view of headgear similar to that shown in FIG. 2-1 having a straight profile along a lower join line;

FIG. 3-1 is a top view of headgear in a partially assembled state according to an example of the disclosed technology;

FIG. 3-2 is an enlarged detail from FIG. 3-1 showing an overlapping region of headgear components according to an example of the disclosed technology;

FIG. 3-3 is enlarged detail from FIG. 3-1 showing another overlapping region of headgear components according to an example of the disclosed technology;

FIG. 3-4 illustrates the shape of a sonotrode or anvil for ultrasonically welding the overlapping region of FIG. 3-3 according to an example of the disclosed technology;

FIG. 3-5 illustrates the shape of a sonotrode or anvil for ultrasonically welding the overlapping region of FIG. 3-2 according to an example of the disclosed technology;

FIGS. 3-6 and 3-7 show headgear components nested in a sheet of material according to an example of the disclosed technology;

FIG. 3-8 shows a top strap of the headgear of FIG. 3-1 according to an example of the disclosed technology;

FIG. 3-9 shows a bottom strap of the headgear of FIG. 3-1 according to an example of the disclosed technology;

FIG. 4-1 is a top view of a headgear section including three components joined by ultrasonic welding according to an example of the disclosed technology;

FIG. 4-2 is a cross-sectional view along the line A-A of FIG. 4-1;

FIG. 4-3 is a cross-sectional view of another example of a headgear section along a line similar to line A-A of FIG. 4-1;

FIGS. 4-4 and 4-5 are cross-sectional views of headgear having a spacer fabric cushion layer;

FIG. 4-6 is an alternative configuration of a headgear section having three components joined by ultrasonic welding according to another example of the disclosed technology;

FIG. 4-7 is a cross-sectional view of headgear components welded together and reinforced with seam reinforcing tape;

FIG. 4-8 is an alternative configuration of a headgear section having three components and seam tape for flexibility joined by ultrasonic welding according to another example of the disclosed technology;

FIG. 5 is a top view of a headgear section including a plurality of straps joined by ultrasonic welding according to an example of the disclosed technology;

FIG. 6 is a top view of a headgear section including a plurality of components joined by ultrasonic welding according to an example of the disclosed technology;

FIG. 7-1 illustrates a headgear section including a rounded edge according to an example of the disclosed technology;

FIG. 7-2 is a side view of the headgear section of FIG. 7-1;

FIG. 8-1 is a partial perspective view of a strap including hook material ultrasonically joined to the strap according to an example of the disclosed technology;

FIG. 8-2 is a cross-sectional view along the line B-B of FIG. 8-1;

FIG. 9 is a partial perspective view of a component including a more rigid less flexible member and a more flexible less rigid member joined by ultrasonic welding according to an example of the disclosed technology;

FIG. 10-1 is a perspective view of a comfort pad having sections joined by ultrasonic welding according to an example of the disclosed technology;

FIG. 10-2 is a side view of the comfort pad of FIG. 10-1;

FIG. 11-1 is a side view of a comfort pad according to another example of the disclosed technology;

FIG. 11-2 is a side view of the comfort pad of FIG. 11-1 attached to a headgear strap according to an example of the disclosed technology;

FIG. 11-3 is a top view of the comfort pad of FIG. 11-1;

FIGS. 12-1 to 12-5 illustrate a method of forming a mask assembly utilizing ultrasonic welding according to an example of the disclosed technology;

FIG. 13-1 illustrates a process of ultrasonically welding two components to form a space between the components according to an example of the disclosed technology;

FIG. 13-2 is a side view of a headgear section including a pocket and a rigidizer to be disposed in the pocket according to an example of the disclosed technology;

FIG. 13-3 is a front view of a headgear section including a rigidizer according to an example of the disclosed technology;

FIG. 13-4 is a front view of two components ultrasonically welded to form a space therebetween;

FIGS. 13-5 and 13-6 illustrate a curved profile strap with a rounded edge profile near the patient side in the relaxed condition and the compressed condition, respectively;

FIG. 15-1 is a side view of a softer component ultrasonically welded to another component to form a softer patient interface according to an example of the disclosed technology;

FIG. 16-1 is a top view of a headgear section including a plurality of components ultrasonically welded according to an example of the disclosed technology; and FIG. 16-2 illustrates a process of nesting headgear components in a sheet of material to increase yield.

DETAILED DESCRIPTION OF ILLUSTRATED EXAMPLES

The following description is provided in relation to several examples which may share common characteristics and features. It is to be understood that one or more features of any one example may be combinable with one or more features of the other examples. In addition, any single feature or combination of features in any of the examples may constitute an additional example or examples.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

1. Headgear

Some of the figures illustrate headgear according to examples of the disclosed technology. In the illustrated examples, headgear is adapted to be removably attached to a mask to hold and maintain the mask in a desired position on a patient's face. While headgear may be illustrated independently and unassociated with a mask used for treatment of SDB (e.g., by pneumatically splinting the patient's airways with gas pressurized in the range of about 2-30 cm $H_2O$ (typically 8-12 cm $H_2O$)), it should be appreciated that each headgear may be adapted for use with any suitable mask such as, for example, full-face mask, nasal mask, mouth mask, nozzles or puffs, nasal prongs and the like, with any suitable configuration (e.g., with or without forehead support).

Also, it should be appreciated that the headgear may be used with a new mask or the headgear may be retrofit to an existing mask.

2. Ultrasonic Welding Process

Ultrasonic welding may be used to join a variety of headgear, mask and accessory components. This process may enhance comfort, fit and/or performance of the joined components and/or associated devices. A component may be a single layer component such as, for example, textile and fabric or a composite or multiple layer component (e.g., fabric and foam composite, coated fabric, a fabric and membrane laminate, or outer fabric layers with an inner spacer fabric). Further, a component may be a strap, some other headgear component, a mask component, an accessory component, etc.

FIGS. 1-1 to 1-5 illustrate a method of joining components by ultrasonic welding according to an example of the disclosed technology. Components may be joined along their length (as shown in FIGS. 1-1 to 1-5), or may be stacked and ultrasonically welded one on top of the other as will be described later.

Figure 1:
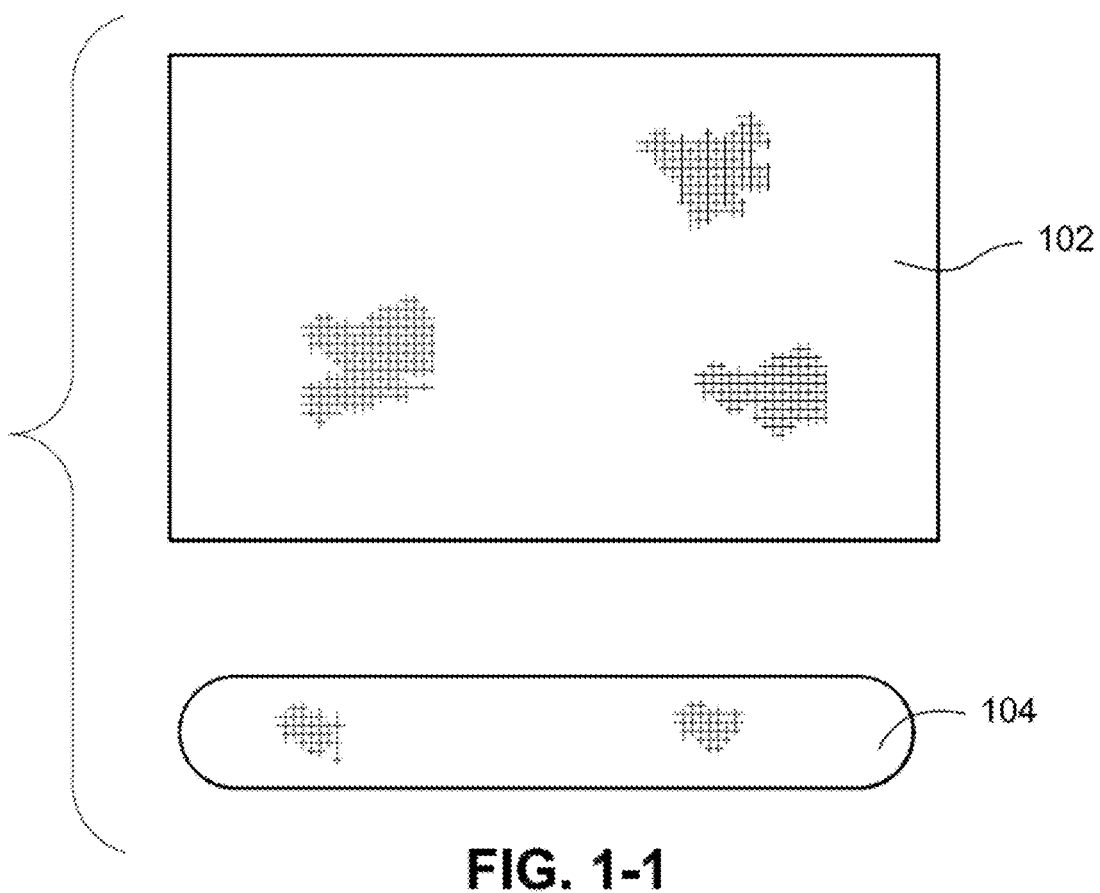
FIGS. 1-1 to 1-5 illustrate a process of joining components by ultrasonic welding according to an example of the disclosed technology.
Figures 1, 2:
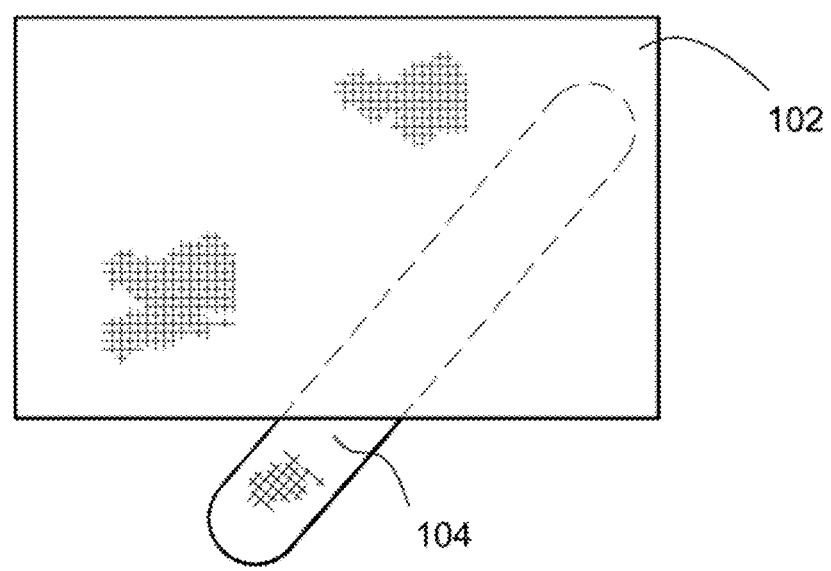
Figures 1, 2, 3:
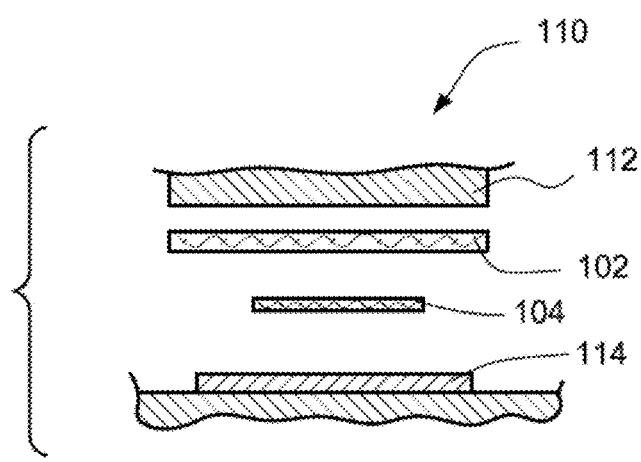

FIG. 1-1 illustrates a first component 102 and a second component 104 which are overlapped and placed in an ultrasonic welding tool 110, as shown in FIGS. 1-2 and 1-3. As seen in FIG. 1-3, the ultrasonic welding tool 110 includes a sonotrode 112 and a knife plate 114. The sonotrode 112 produces ultrasonic vibration that welds the components 102, 104 as one skilled in the art will understand. The vibration of the sonotrode 112 may create energy which may then be converted into heat energy by an anvil. The anvil may be a perimeter knife line 116 on knife plate 114 as shown in FIG. 1-4. The knife line 116 may then cut and seal a component, the cutting achieved by the sharp edge and the sealing achieve by the heat. The knife line 116 may be a single line of sharp edge or may be a series of small sharp edges (e.g. for spot welding). The knife plate is pre-shaped with a knife line in accordance with a desired shape to be cut from the components 102, 104. Thus, as the knife plate acts against the sonotrode, first component waste 132 and second component waste 134 are removed in a single cut and seal operation, resulting in a single component combination 122, as shown in FIG. 1-5. The knife plate 114 and the sonotrode 112 ultrasonically weld the first and second components thereby forming a joint 124 that connects the first component 102 and the second component 104. The knife plate 114 also shapes the components 102, 104 (simultaneously as it formed the joint 124), and in this example, shapes components 102, 104 into headgear straps. As mentioned earlier, an advantage of this process is that the components 102, 104 can be overlapped in the ultrasonic welding tool 110 with no need to align the edges of the components. The ultrasonic welding tool 110 removes the overlapping second component waste 134 and joins the components such that the resulting combination has a constant or uniform thickness— hence the term 'flush joint' as the components joined together are flush or in line with one another rather than there being added thickness. It should be noted that more than two components may be ultrasonically welded in this manner. The resulting ultrasonic 'butt' or 'flush' joint may then be reinforced by any one or more of means of stitching, tacking, overmoulding with a polymer, spot welding, applying a thin fabric with an adhesive backing, applying hot-melt seam tape, and/or other method of reinforcement.

2. Ultrasonic Welding Joint

The ultrasonic welding process may be arranged to provide a joint of the connected components, such as a flush joint. When stitching two components together, the components must be overlapped, and hence the final thickness of the stitched portion is the thickness of the two components added together. Unlike stitching, ultrasonically welded components may be overlapped in the tool and then welded, which results in a melted portion at the point contact between the components that are welded. The melted portion forms a joint that connects the components. The portion of the first component that was overlapped onto the second component may be discarded so the remaining portion of the first component abuts the second component and forms a flush or abutting joint. The thickness of the joint may be no thicker than the thickness of the first or second component or may be less than both combined. This is best shown in FIG. 1-5, where the second component waste 134 was the overlapping portion and is subsequently discarded, and the first component 102 and a second component 104 abut one another at joint 124 to form a single component combination 122 in a flush, homogenous, and/or flat manner.

An advantage of the ultrasonic welding process is that a flush or butt joint does not increase the thickness of the components at the joint and is visually appealing, unlike stitching where components must be overlapped and which results in an uneven thickness. Even if the edges of the two or more components are butted together and stitched without any or substantial overlapping, the stitches will create a rougher, stiffened and raised joint. Further, the ultrasonic flush or butt joint may result in a smooth connection that may reduce skin irritation, chaffing or facial marking, even when reinforced with seam reinforcement tape. An advantage of using an overlapped ultrasonic weld variation is that multiple components may be joined in a single machine in one operation. Another advantage of ultrasonic welding is that multiple components may be situated in the ultrasonic welding machine in an overlapping manner without aligning the edges of the components, as the edges of the joint will be neatened during the cut and sealing process and the excess material may be removed.

Furthermore, the ultrasonic welding process may be designed such that the joint is embodied as a thinned region or thinned portion between the components. The thinned region may function as a flex point or hinge (e.g., a living hinge) to provide increased flexibility where desired. The flex point or hinge may be reinforced using hot-melt seam tape, or a thinner fabric layer with an adhesive backing, or other reinforcement methods.

3. Ultrasonic Welding Along Component Length

Components may be joined along their length to create a single component (e.g., straps joined to form headgear).

In an example of the disclosed technology, headgear 200, shown in FIG. 2-1, may be formed by ultrasonically welding various components. Headgear 200 includes two lateral crown sections 210 and an upper crown section 212 forming a ring-like shape configured to fit the crown of a patient's head. Top straps 204 and bottom straps 206 depend from the crown section and are adapted to hold a mask in place on a patient's face. The top straps 204 may include adjustment members 205 (e.g., hook material) for securing the straps. Similarly, the bottom straps 206 may include adjustment members 207 (e.g., hook material). The lateral crown section 210, the upper crown section 212, the top straps 204 and the bottom straps 206 may be ultrasonically welded resulting in joints 222, 224, 236, 238. The joint 222 may interconnect the top strap 204 and both the upper crown section 212 and the lateral crown section 210. The joint 224 may interconnect the lateral crown section 210 and the upper crown section 212. The bottom straps 206 may be connected such that the joint 238 interconnects the bottom straps. The joint 236 may interconnect the lateral crown section 210 and the bottom straps 206. Accordingly, as illustrated the headgear may be formed with welded tri-joints such as in the case of joints 222, 224 where three components abut. Similarly, welded bi-joints may be formed as in the case of joint 238. Of course, additional joints may be created (e.g., quad-joints, etc.).

As mentioned earlier, the joints 222, 224, 236, 238 may be constructed as a thinned region to encourage bending.

Such a hinge feature may permit the headgear to better accommodate the shape of a patient's head. The joint 238 may provide a more flexible region as compared to the curved joint 236, since the joint 238 extends substantially linearly thereby providing a linear axis about which the bottom straps 206 may pivot. The joint 236 extends in a nonlinear or curved manner which may provide a lower level of flexibility. The curvature in the joint 236 may also determine the direction of flexion. For ease of manufacturability, the join line 236 might be substantially straight, as shown in FIG. 2-2. A combination of linear and nonlinear joints, such as at the connection of the lateral crown section 210, the upper crown section 212 and the top straps 204, may be utilized to achieve a desired level of flexibility and direction of flexion, as well as a desired level of three-dimensional shaping to a component made up of a series of parts which were originally a flat material (such as fabric or paper, for example). Such shaping may include darts, tucks, gathers, or a curved seam.

Referring to FIG. 3-1, in another example of the disclosed technology, headgear 300 may be formed by ultrasonically welding various components. Headgear 300 is similar to headgear 200 described above and includes a crown section formed of two lateral crown sections 310 and an upper crown section 312. The top straps 304 include adjustment members 305 (e.g., hook material) and bottom straps 306 include adjustment members 307 (e.g., hook material). The top and bottom straps 304, 306 may also include unbroken loop material on an outer surface to cooperate with the adjustment members.

The lateral crown sections 310, the upper crown section 312, the top straps 304 and the bottom straps 306 may be made of a spandex or elastane/foam composite, or could be formed of other suitable materials (such as a 3D spacer fabric or a double-knit interlock fabric). These components may be cut from a sheet of material (e.g., flame laminated), or cut from a roll of narrow fabric strap and then thermoformed and ultrasonically welded to create rounded edges before being ultrasonically welded together. The components may have a geometry that allows them to be nested on the sheet to increase yield e.g. the geometry may be substantially linear.

FIG. 3-2 is an enlarged detail from FIG. 3-1 showing an overlapping region 324 of the lateral crown section 310, the upper crown section 312 and an upper strap 304. Specifically, as seen in FIG. 3-2, portions of upper crown section 312 and the upper strap 304 overlap and portions of the lateral crown section 310 and upper strap 304 also overlap as shown by the shaded regions. These members may be placed in an ultrasonic welding tool 110, as described above, for ultrasonic welding. The ultrasonic welding tool 110 may weld together overlapping portions by applying ultrasonic vibrations to the anvil 324 in order to join the overlapping components of the lateral crown section 310, the upper crown section 312 and an upper strap 304 in one process and my form an overlapped tri-joint. Similarly, referring to FIG. 3-3, the ultrasonic welding tool will join an edge of the lateral crown section 310 and an edge of the bottom strap 306 at the overlapping region 326 and may form an overlapped bi-joint.

The joints in the headgear 300 may be arranged to provide flexibility or areas of rigidity in the same manner as described above with regard to the headgear 200.

Figures 1, 2, 3, 4:
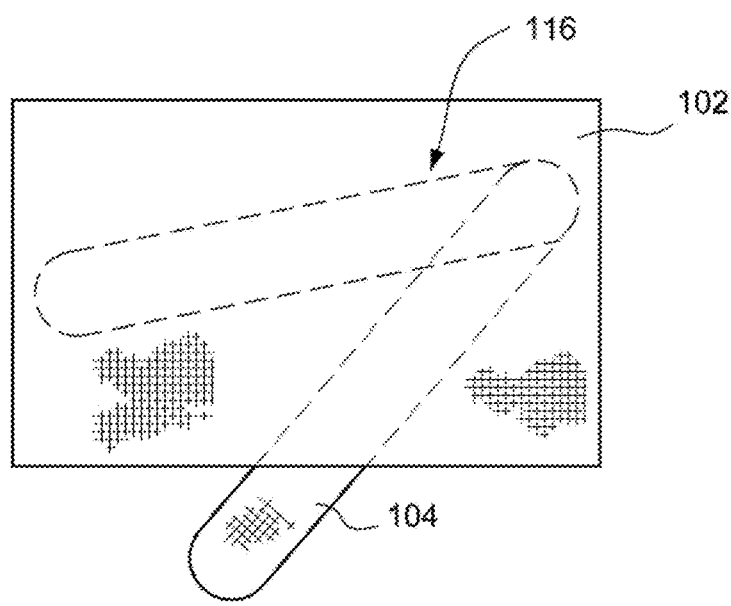

Referring to the anvil tool shown in FIG. 3-4, adapted to create overlapping region 326, in an example, D1 may be about 11.7-17.7 mm, e.g., 14.7 mm, D2 may be about 10.9-16.9 mm, e.g., 13.9 mm, D3 may be about 18.15-28.15 mm, e.g., 23.15 mm, D4 may be about 7-11 mm, e.g., 9.0 mm, D5 may be about 2.5-5.5 mm, e.g., 4.0 mm, D6 may be about 1.2-2.0 mm, e.g., 1.6 mm, the radius of curvature R1 may be about 74.6-114.6 mm, e.g., 94.6 mm, the radius of curvature R2 may be about 0.8-1.2 mm, e.g., 1.0 mm, the radius of curvature R3 may be about 70-110 mm, e.g., 90 mm, the radius of curvature R4 may be about 2.3-3.7 mm, e.g., 3.0 mm, the radius of curvature R5 may be about 3.1-4.9 mm, e.g., 4.0 mm, and the radius of curvature R6 may be about 1.9-3.1 mm, e.g., 2.5 mm.

Figures 1, 2, 3, 4, 5:
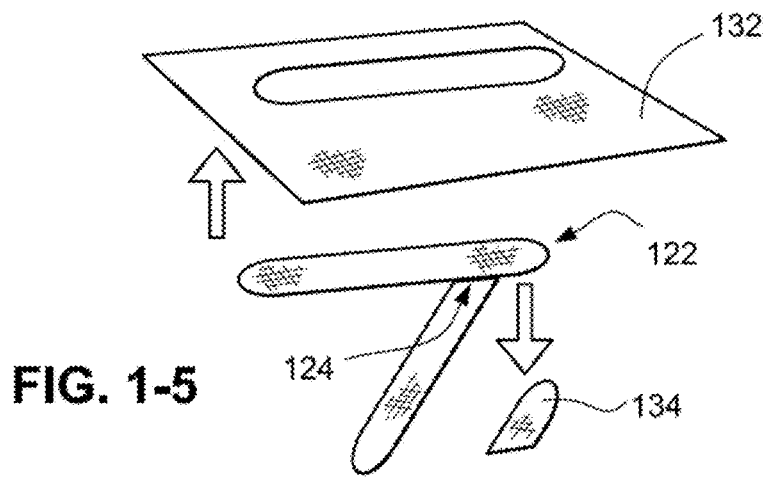
Figures 1, 2:
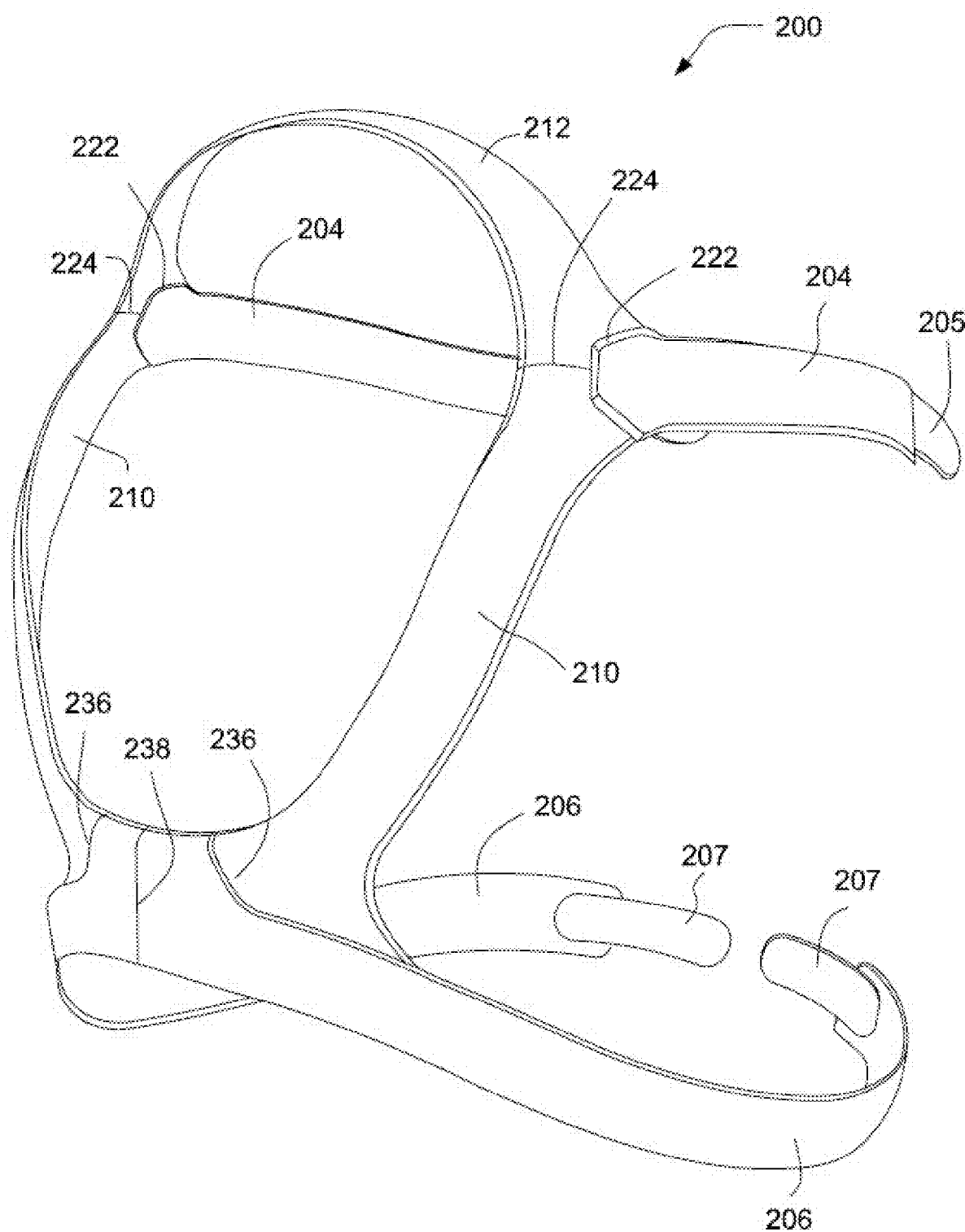
Figure 2:
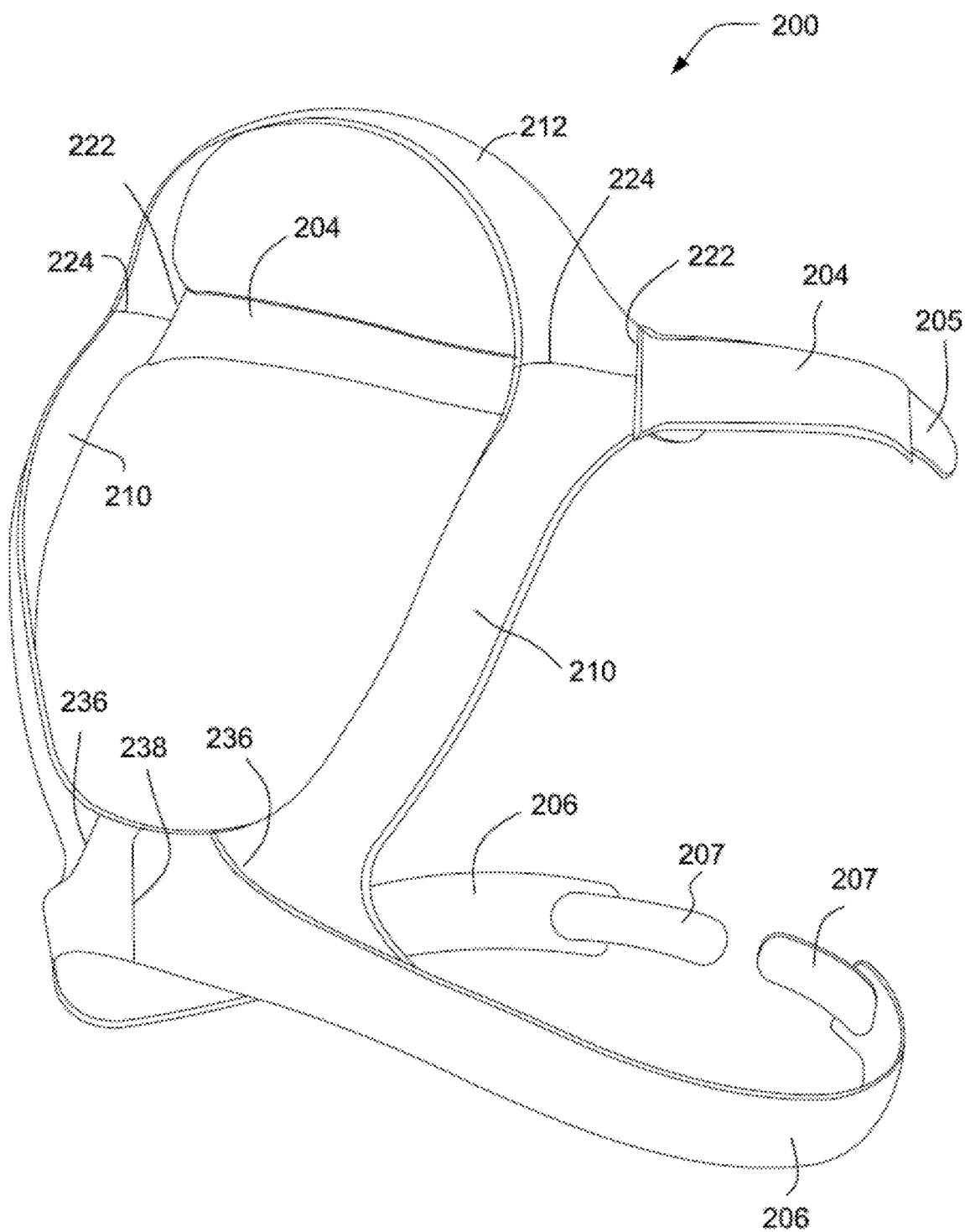

Referring to the anvil tool shown in FIG. 3-5, adapted to create overlapping region 324, in an example, D1 may be about 7.15-12.15 mm, e.g., 9.65 mm, D2 may be about 10.75-16.75 mm, e.g., 13.75 mm, D3 may be about 23.55-37.55 mm, e.g., 30.55, D4 may be about 3.75-6.25 mm, e.g., 5.0 mm, the radius of curvature R1 may be about 1.25-2.75 mm, e.g., 2.0 mm, and the angle a1 may be about 20.0-40.0°, e.g., 30°.

The area of the anvil tools described in FIG. 3-4 and FIG. 3-5 may be patterned with a series of raised areas (such as squares, or dots, or diamonds) which may function to focus the energy of the vibrating ultrasonic sonotrode, thus generating heat at the tip of these raised areas, this heat then melts the material of the components being joined, thus fusing the parts together.

FIG. 3-6 illustrates lateral crown sections 310 situated on a sheet of material from which they are cut. The lateral crown sections 310 are arranged on the sheet to maximize yield. In an example, D1 may be about 99.43-179.43 mm, e.g., 139.43 mm, D2 may be about 58.8-98.8 mm, e.g., 78.8 mm, and D3 may be about 30.0-50.0 mm, e.g., 40.0 mm.

FIG. 3-7 illustrates upper crown sections 312 situated on a sheet of material from which they are cut. The upper crown sections 312 are arranged on the sheet to maximize yield. In an example, D1 may be about 157.97-257.97 mm, e.g., 207.97 mm, D2 may be about 27.43-47.43 mm, e.g., 37.43 mm, and D3 may be about 20.0-40.0 mm, e.g., 30.0 mm.

FIG. 3-8 illustrates top straps 304 situated on a sheet of material from which they are cut. The top straps 304 are also arranged on the sheet to maximize yield. In an example, D1 may be about 187-287 mm, e.g., 237 mm, D2 may be about 14-22 mm, e.g., 18 mm, D3 may be about 20-36 mm, e.g., 28 mm, and D4 may be about 17.28-27.28 mm, e.g., 22.28 mm.

FIG. 3-9 illustrates bottom straps 306 situated in on a sheet of material from which they are cut. Similarly, the bottom straps 306 are arranged on the sheet to maximize yield. In an example, D1 may be about 232-372 mm, e.g., 302 mm, D2 may be about 14-22 mm, e.g., 18 mm, and D3 may be about 20-36 mm, e.g., 28 mm.

3.1 Examples

In the following sections, further techniques, arrangements and/or benefits of ultrasonic welding according to examples of the disclosed technology are described. Such techniques and/or arrangements may enhance comfort, fit and/or performance of headgear, masks and/or accessories. It is noted that any feature described, above or below, in relation to headgear may also be usable with a mask and/or accessory item, and vice versa.

3.1.1 Even Surfaces at Join

Headgear 400 includes a first headgear component 402, a second headgear component 404 and a third headgear component 406, as shown in FIGS. 4-1 and 4-2. The headgear components may be straps. The headgear components 402, 404, 406 are joined by ultrasonic welding at a point where all three components meet, in a cut and seal process that creates a butt joint or welded butt tri-joint (i.e. joint of three components).

As shown in FIG. 4-2, the first headgear component 402 may include an outer textile 402-1, an inner textile 402-2 and a cushion layer (e.g., foam or 3D spacer fabric) 402-3. The second headgear component 404 may include an outer textile 404-1, an inner textile 404-2 and a cushion layer (e.g., foam or spacing filaments) 404-3.

As illustrated in FIG. 4-2, the ultrasonic welding process results in a joint 410 that interconnects the first and second headgear components 402, 404 and permits top (402-1, 404-1) and bottom (402-2, 404-2) surfaces of the components to be aligned thereby providing a smooth, even butt joint which enhances patient comfort. In the alternative, a stitched butt joint would result in the first and second components 402, 404 being connected with a raised area of thread (e.g., sewn with a zig-zag stitch) which provides an uneven, rough surface that may be uncomfortable to the patient. Alternatively, a flat lap seam that covers the raw edges of the fabric could be stitched here; this structure may be less desirable especially when used with cushioned fabrics as a flat lap seam is not truly flat, rather it consists of four fabric layers due to a folding and interlocking process. An exemplary lap seam can be seen in GB 2482990, which his hereby incorporated by reference in its entirety. While it is neat, the seam creates a thicker surface (i.e. thickness of the joint is greater than the thickness of the materials) which may cause patient discomfort, therefore a butt or simple overlap ultrasonic seam or weld is most desirable.

Referring to FIG. 4-3, even if the first and second components 402, 404 have a different thickness, in the case of a thicker crown strap being ultrasonically welded to a front strap, the inner textile layers or patient interface surfaces 402-2, 404-2 may be aligned to provide a smooth, even patient interface. That is, the patient side surface of the joined components may be welded so that these surfaces are flush, while the opposing surfaces are not flush.

An alternative example is shown in FIG. 4-4 which illustrates a first headgear component 402 that includes an outer textile 402-1, an inner textile 402-2 and a spacer fabric cushion layer 402-4 and a second headgear component 404 includes an outer textile 404-1, an inner textile 404-2 and a spacer fabric cushion layer 404-4. FIG. 4-5 illustrates this configuration using components of different thicknesses, D1 and D2, similar to that shown for FIG. 4-3.

Figures 2, 3:
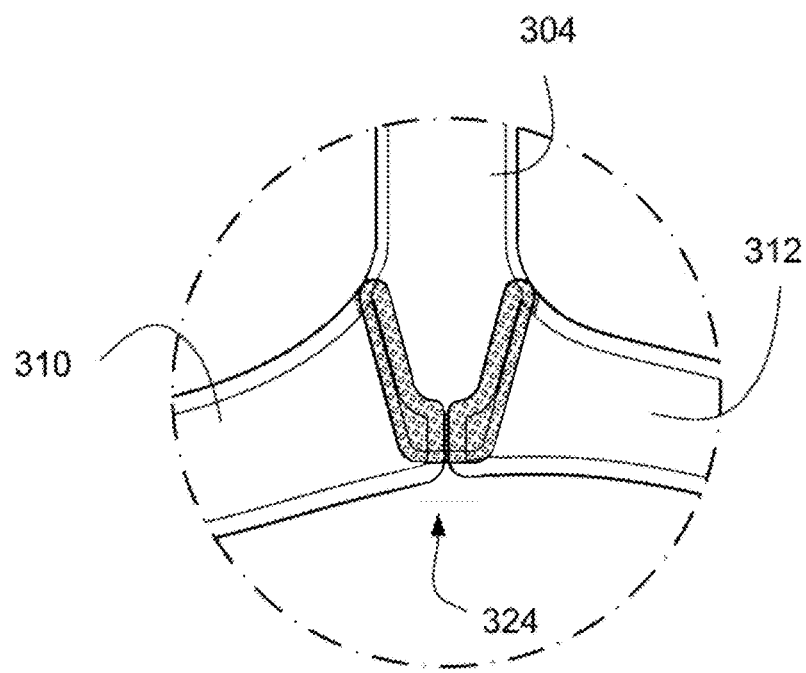
Figure 3:
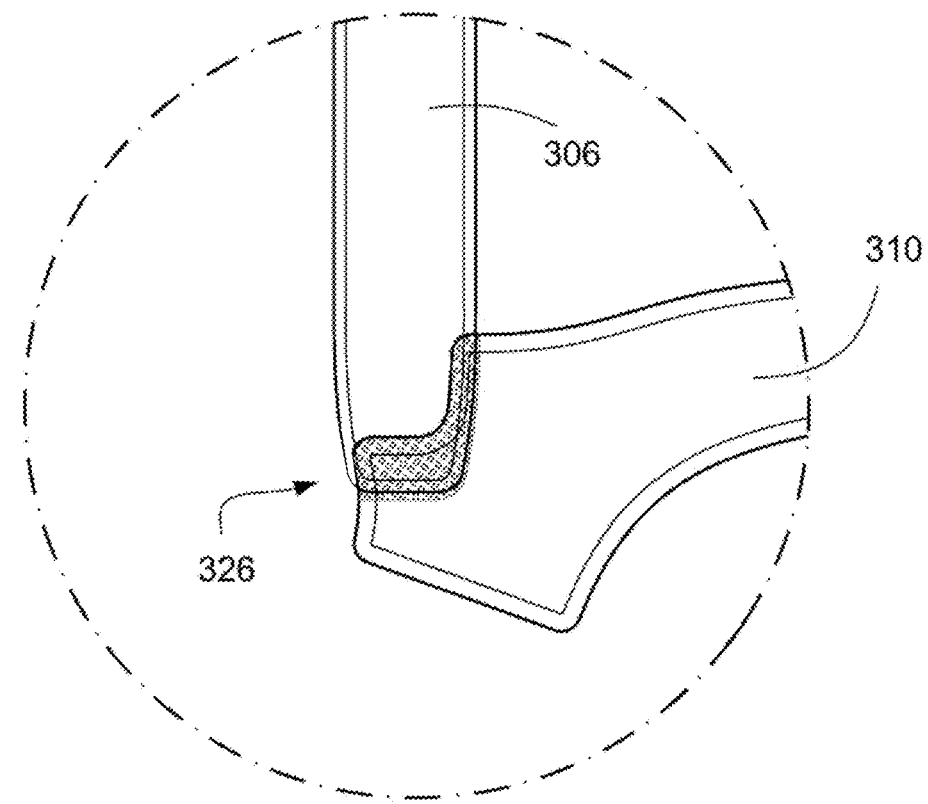
Figures 3, 4:
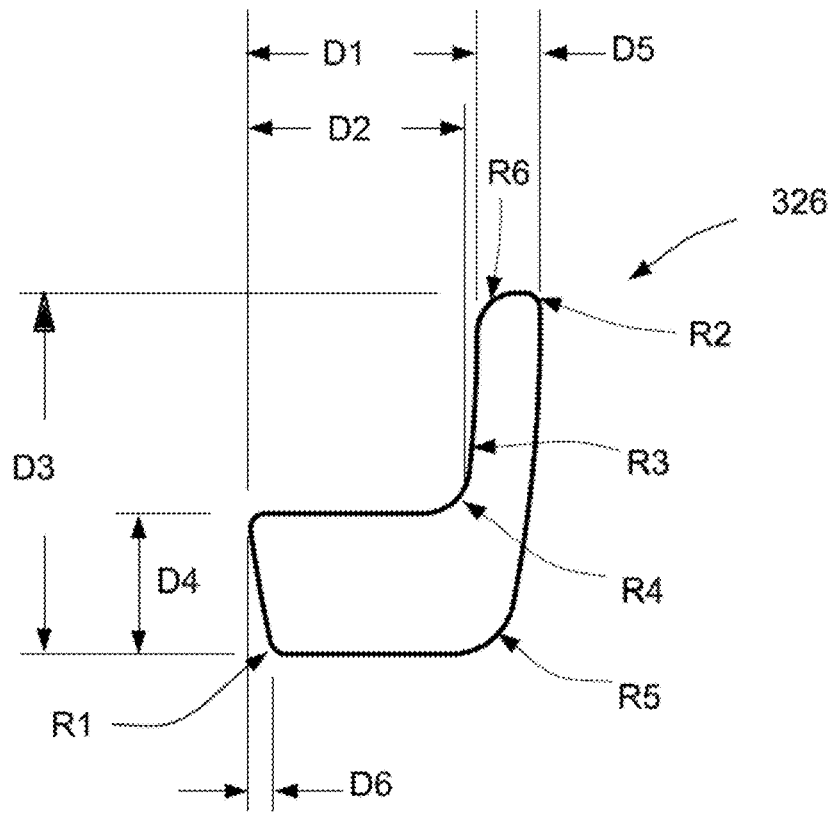
Figures 3, 4, 5:
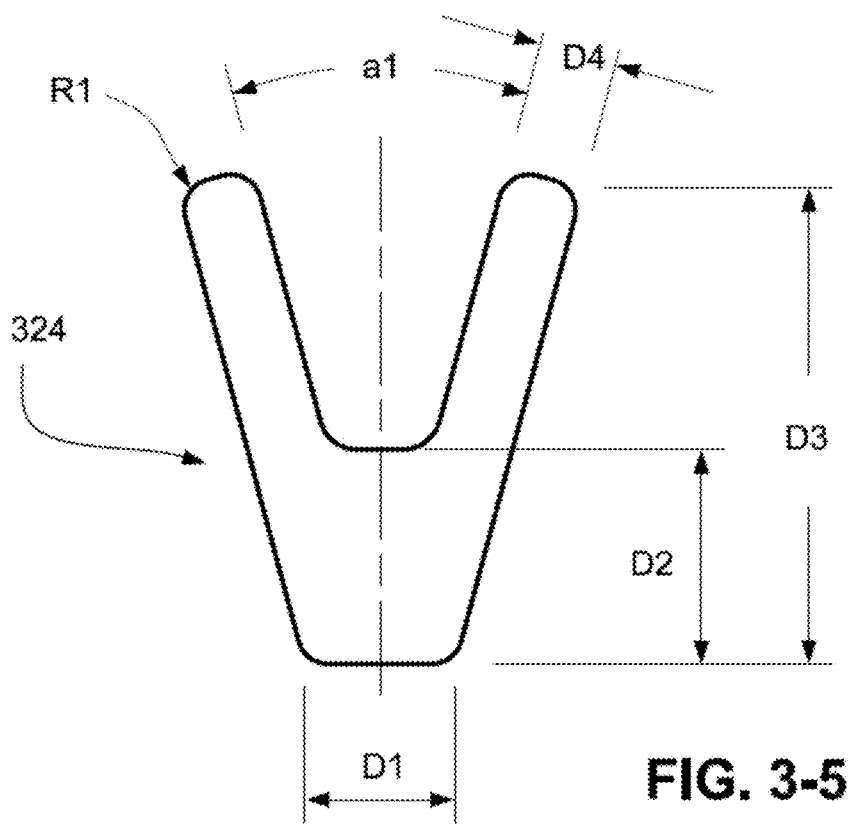
Figures 3, 4, 5, 6:
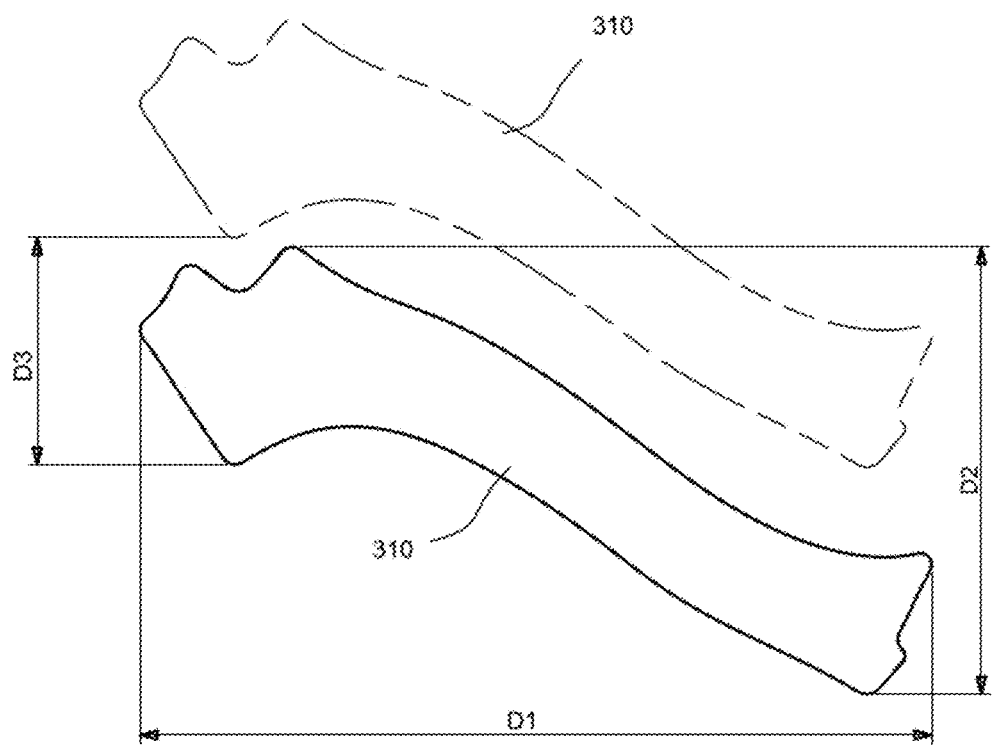

Additionally, headgear 400 may be configured with bi-joints shown in FIG. 4-6 to include a first headgear component 402 and a third headgear component 406 joined to two ends of a second head gear component 404 instead of meeting a triple point as shown in FIG. 4-1 as a tri-joint. As seen in FIG. 4-6, the first headgear component 402 and the third headgear component 406 do not directly contact one another and are instead joined to second headgear component 404.

As shown in FIG. 4-7, in at least some examples, the resulting butt weld joint 410 between two components 402, 404 may be reinforced with seam tape. One way of reinforcing the weld while maintaining the low profile flush surface is to laminate or cover it with a tape 420 formed of a thermoplastic film or sheet. In some examples, tape 420 is formed of a seam reinforcing tape such as Sewfree® tapes provided by Bemis. The tape may serve to reinforce seams created by ultrasonic or laser equipment. The ultrasonically bonded seam may require additional strength and may not be not be entirely waterproof. Reinforcing tapes may be applied to the seams to create superior seam strength and further weatherproof the joint without adding significant bulk. In some examples, the tape may have a thickness of between about 0.1 mm and about 1 mm. The tape may also be formed of multi-layered thermoplastic adhesive film or from coated fabrics. In this manner, tapes may be applied to the joint to prevent water from soaking through the joint and may be applied by using a hot air taping machine. Tape 420 may also be formed of heat seal seam tape.

As shown in FIG. 4-7, in at least some examples, the resulting butt weld joint 410 between two components 402, 404 may be reinforced with seam tape. One way of reinforcing the weld while maintaining the low profile flush surface is to laminate or cover it with a tape 420 formed of a thermoplastic film or sheet. In some examples, tape 420 is formed of a seam reinforcing tape such as Sewfree® tapes provided by Bemis. The tape may serve to reinforce seams created by ultrasonic or laser equipment. The ultrasonically bonded seam may require additional strength and may not be not be entirely waterproof. Reinforcing tapes may be applied to the seams to create superior seam strength and further weatherproof the joint without adding significant bulk. In some examples, the tape may have a thickness of between about 0.1 mm and about 1 mm. The tape may also be formed of multi-layered thermoplastic adhesive film or from coated fabrics. In this manner, tapes may be applied to the joint to prevent water from soaking through the joint and may be applied by using a hot air taping machine. Tape 420 may also be formed of heat seal seam tape.

Additionally, in some examples, tape is overlaid with a thin fabric layer 430 having a thickness of about 0.1 mm and about 1 mm to maintain a desirable soft surface finish. Such thermoplastic sheets 430 might be made from, for example: polyurethane (TPU), polyester, polyamide, polyolefin and aliphatic urethanes. These materials may be customised to provide the optimum performance characteristics for specific applications, and can be produced in a range of colours, opacities, and surface finishes required for the end use of patient interface equipment for the treatment of sleep disordered breathing, such as in headgear or a mask arrangement.

As shown in FIG. 4-8, in some examples, in order to create a hinge, headgear components 402, 404, 406 may be placed in an ultrasonic welding tool without first welding them together. The components may be sandwiched together between two pieces of seam tape 420 or heat fusible fabric. The resulting joint may have a thinner bridge in between the headgear pieces that make up a larger component, creating an area of high flexibility 450 that may function as a hinge.

3.1.2 Multiple Vectors

A multiple strap section 500 includes a first strap 502, a second strap 504 and a third strap 506, as shown in FIG. 5. The second strap 504 includes an attachment member 504-1 for connection to headgear or another securing device. The third strap 506 includes a similar attachment member 506-1. V1 and V2 represent respective vectors for the second and third straps 504, 506 and indicate a direction of the force applied to the straps by the headgear or securing device. Although the vector for the first strap 502 is not shown, it will be appreciated from FIG. 5 that the first, second and third straps 502, 504, 506 each have different vectors.

The straps 502, 504, and 506 are overlaid in an ultrasonic welding tool to form a first joint 510 and a second joint 512. The first joint 510 interconnects the first strap 502 and the second strap 504, while the second joint 512 interconnects the second strap 504 and the third strap 506. Thus, the first, second and third straps 502, 504, 506 can be combined, without a significantly raised structure (as required with stitching), to provide multiple vectors in a multiple strap section 500 having a single thickness. If desired, the straps may have different thicknesses; as described above, the patient interfacing surfaces of the straps may still provide an even contact surface for the patient. The joints may be reinforced on either or both of the patient interface surface of the outer surface of the component by affixing seam tape over the join, that is, by pressing a composite of a thin fabric layer with a layer of heat-activated glue to the joint under a hot plate, heat fusing press, an iron, or a roller with hot air outlet.

3.1.3 Hinge or Flex Point

The ultrasonic welding process may form a joint embodied as a thinned region, where the thickness of the component is smaller than the surrounding portions of the component, such as in a narrow channel on one or both surfaces of the component, which may function as a flex point or hinge (e.g., a living hinge) to provide flexibility where desired.

Turning to FIG. 6, a headgear section 600 includes a first component 602, a second component 604, a third component 606, a fourth component 608 and a fifth component 610. A first joint 622 interconnects the first component 602 and the second component 604. A second joint 624 interconnects the second component 604 and the third component 606. A third joint 626 interconnects the third component 606 and the fourth component 608, and a fourth joint 628 interconnects the fourth component 608 and the fifth component 610.

Joints may be arranged in relation to one another to allow a headgear section to adapt to a particular three-dimensional shape. As shown in FIG. 6, the first joint 622 and the second joint 624 are arranged to intersect and may form an angle there between. Thus, it may allow the first component 602, the second component 604 and the third component 606 to flex in a particular angled manner. The third and fourth joints 626, 628 have a different angled (e.g., non-parallel and non-intersecting) relation allowing the third component 606, the fourth component 608 and the fifth component 610 to flex in a different manner. Intersecting joints and non-intersecting joints provide different methods of flexion. Because many of the joints described above are substantially flat, intersecting joints may be formed of multiple joints at the same location, affording greater variation for the final shape of the headgear. In this manner, it may be possible to overlap multiple components and insert a joint in between an existing joint simply because the joints are flush and thus sit flat. This may be useful when creating a textile mask of a complex shape requiring multiple overlapping joints.

3.1.4 Rolled Edge

Rolled or rounded portions may be ultrasonically welded to flat headgear portions to provide rounded edges which may enhance comfort for the patient and substantially prevent facial marking.

Figures 3, 4, 5, 6, 7:
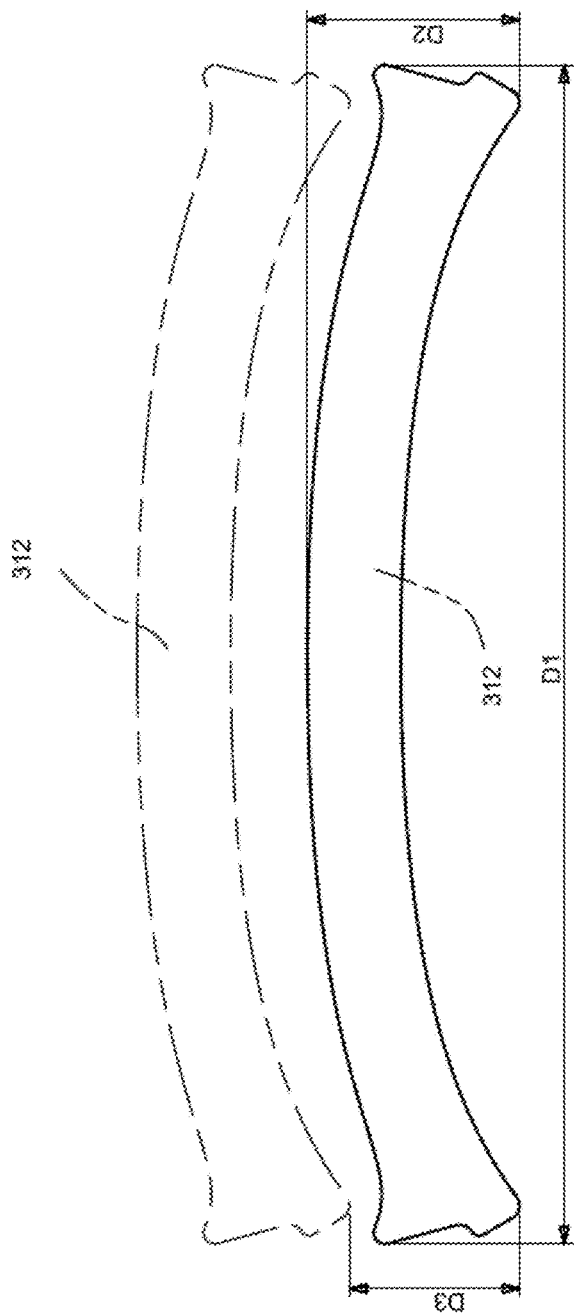

In FIG. 7-1, a headgear section 700 (e.g., a strap) includes a flat portion 702 and rolled portions 704 ultrasonically welded to ends of the flat portion 702. In the illustrated example, the headgear section 700 is a strap. The flat portion may be a soft fabric layer and the rolled portions may be a fabric/foam composite. The flat portion 702 may be a low profile section in order to reduce bulk. The rolled portions 704 prevent edges of the flat portion 702 from contacting the patient's skin 720 which may otherwise cause irritation or facial marking, as shown in FIG. 7-2. Rolled portions 704 may be formed by ultrasonically welding the rolled portion along its edge, which is then ultrasonically welded to ends of the flat portion 702. A joint 712 interconnects the flat portion 702 and the rolled portions 704.

The joint 712 is a low-profile joint such that there are no edges or sharp or raised seams which may degrade comfort. Further, unlike stitching, there are no raised or loose threads above the surface which may irritate the patient.

3.1.5 Nested Fastening Member

Figures 3, 4, 5, 6, 7, 8:
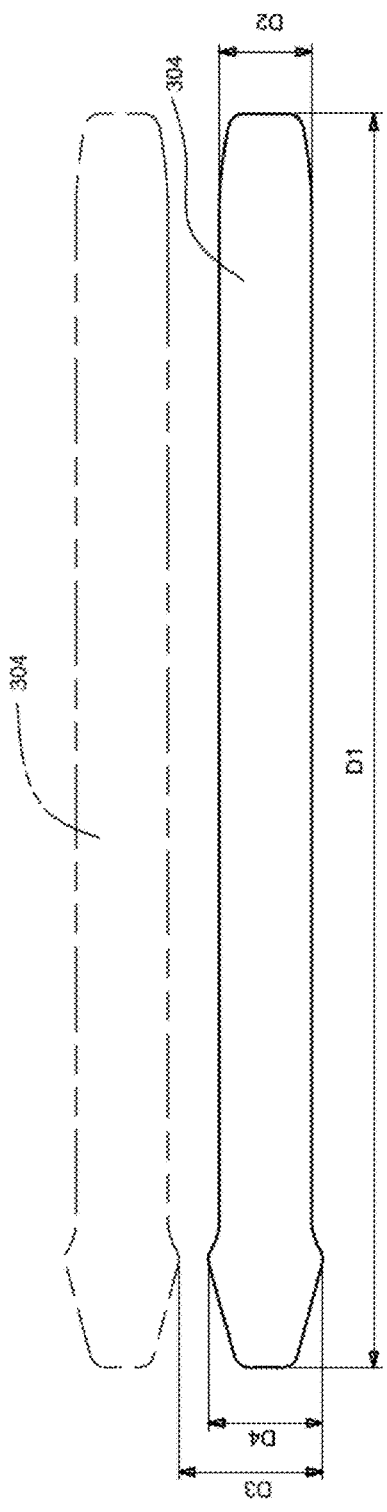

An ultrasonic welding process may be used to nest a fastening member, such as hook material (e.g., VELCRO® brand fasteners), within a strap such that the hook material is recessed in the strap. Referring to FIG. 8-1, a strap 800 and a hook material section 804 may be placed in the ultrasonic welding tool similar to that described in FIG. 1-3. The ultrasonic welding tool may remove a portion of the strap leaving behind a hole 802 in which the hook material is disposed. As shown in FIG. 8-2, the hook material 804 is nested within the hole 802 and is further ultrasonically welded to the strap. Resulting joints 806 interconnect the strap 800 and the hook material 804.

By nesting the hook material within the strap, the likelihood of the hook material 804 abrading the patient's skin or catching the patient's hair is considerably reduced since the hook material is in a plane that is offset from a plane of the remaining part of the strap that contacts the patient's face.

3.1.6 Controlled Flex Region

Figures 3, 4, 5, 6, 7, 8, 9:
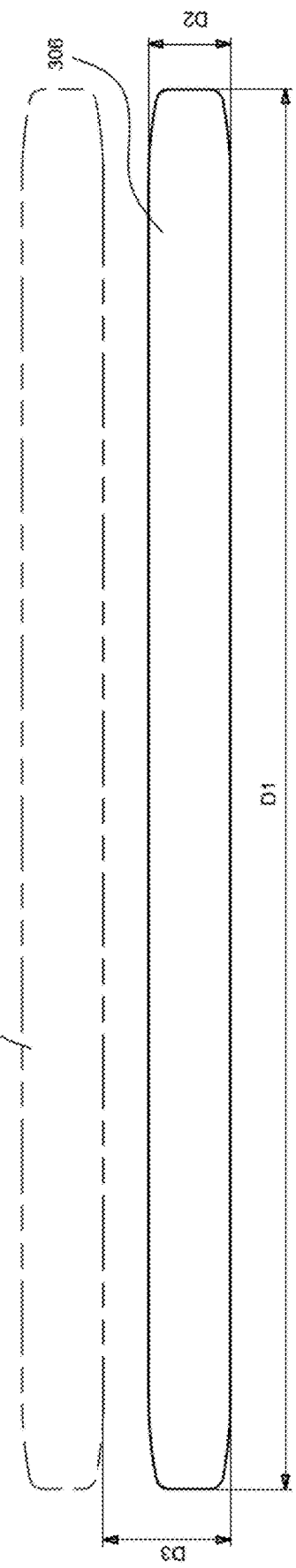
Figures 1, 4:
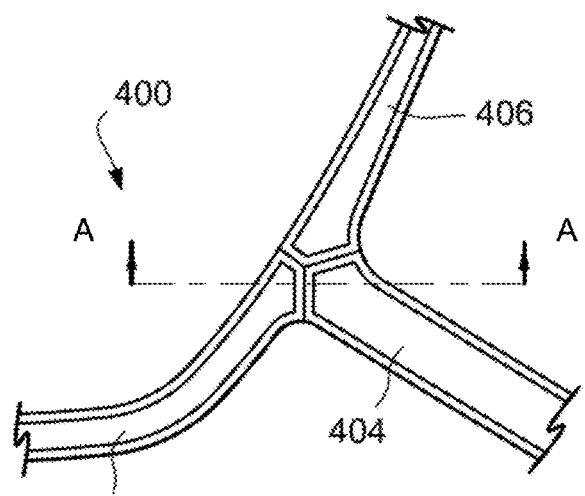
Figures 2, 4:
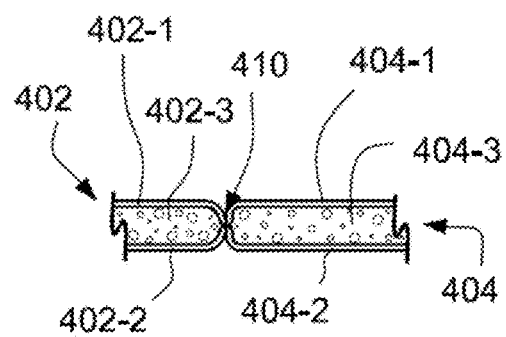
Figures 3, 4:
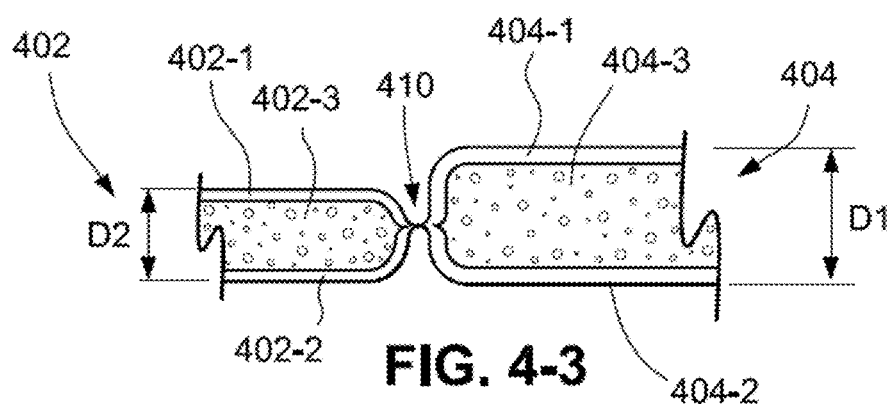
Figure 4:
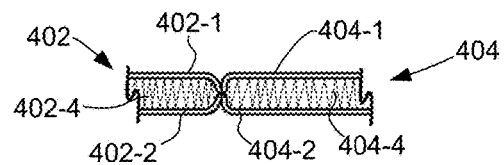
Figures 4, 5:
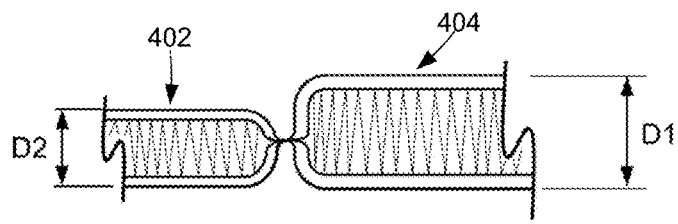
Figures 4, 5, 6:
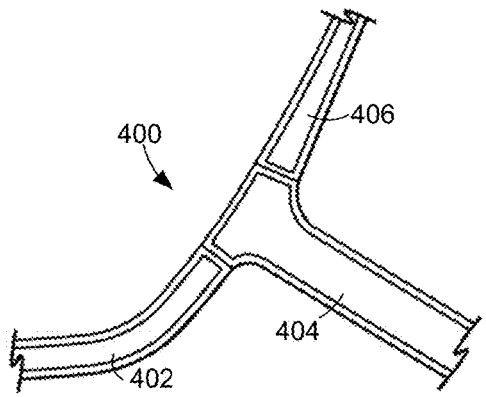
Figures 4, 5, 6, 7:
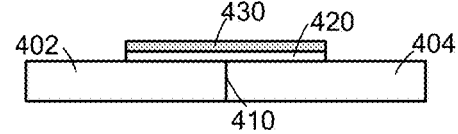
Figures 4, 5, 6, 7, 8:
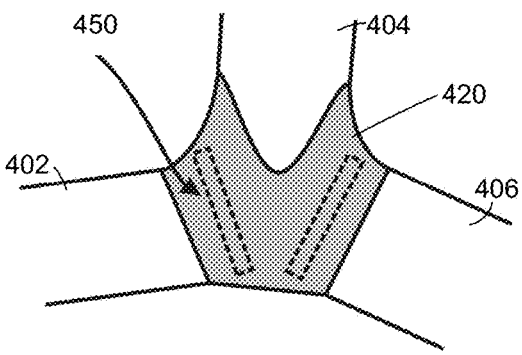
Figure 5:
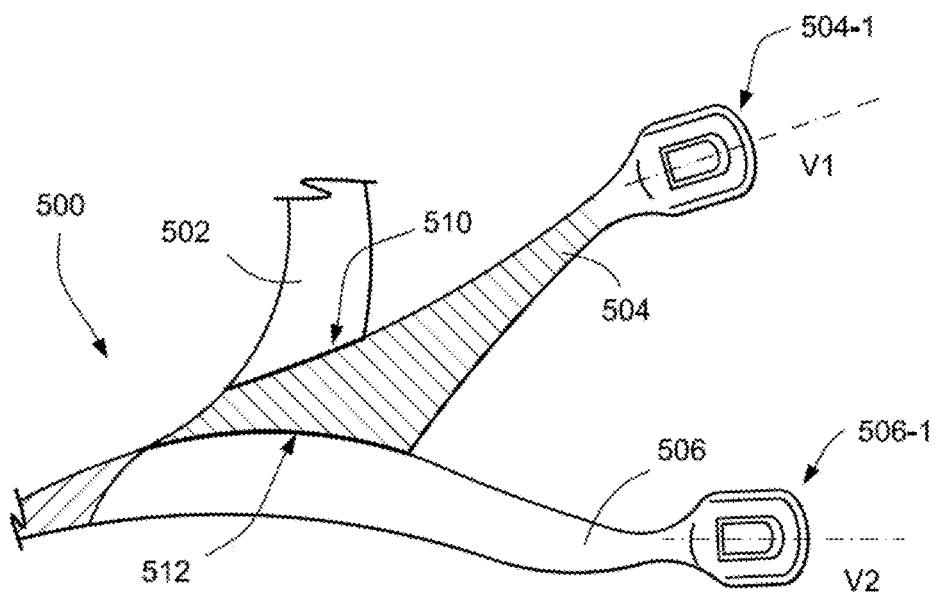
Figure 6:
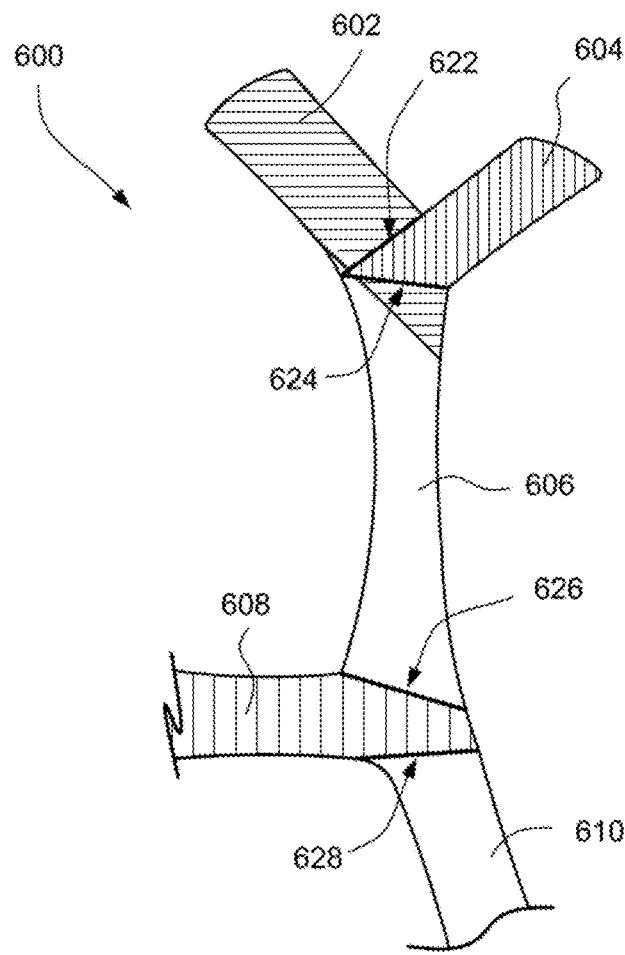
Figures 1, 7:
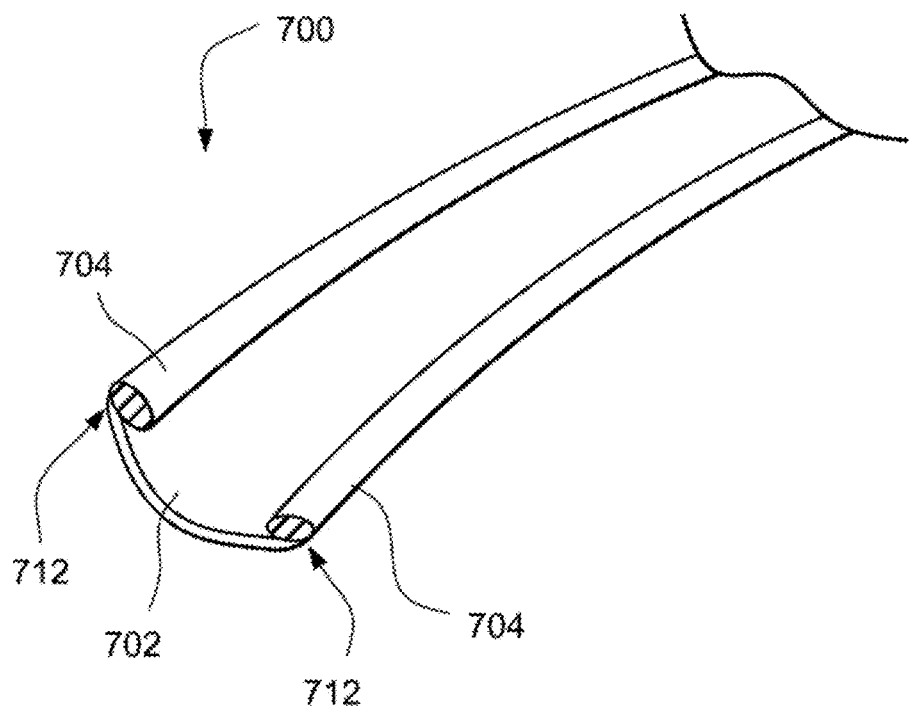
Figures 2, 7:
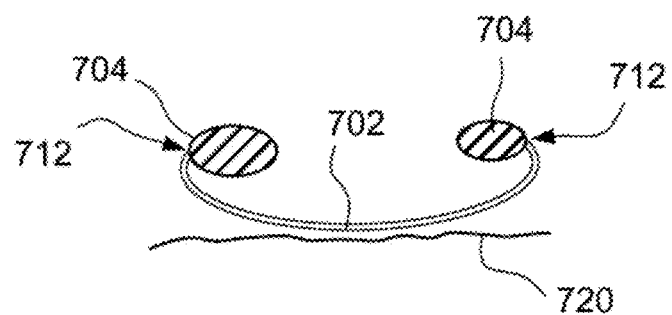
Figures 1, 8:
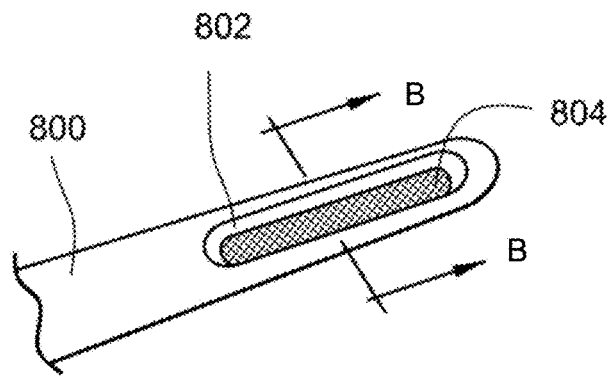
Figures 2, 8:
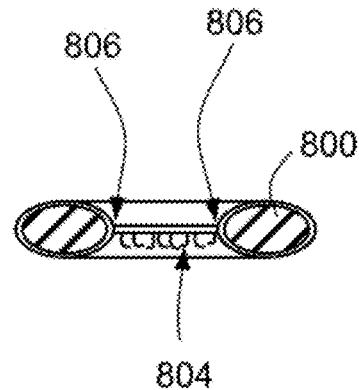
Figure 9:
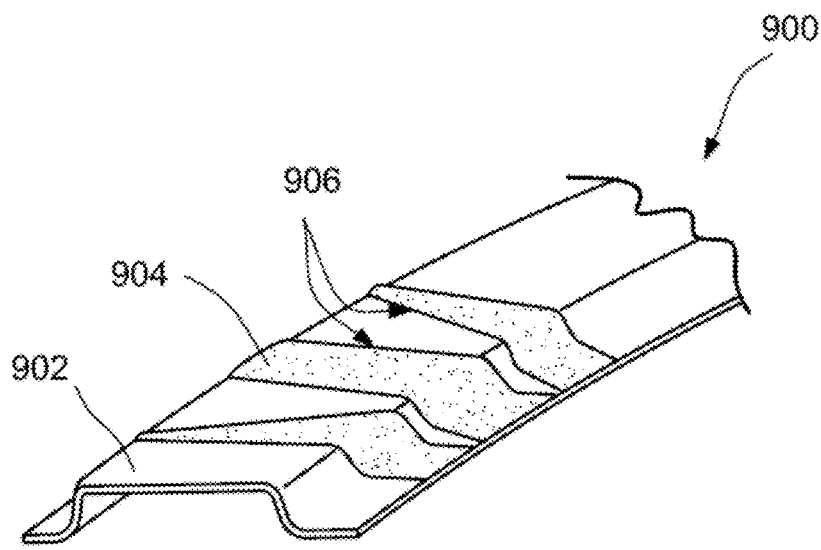

Materials having differing degrees of flexibility may be ultrasonically welded to one another in an alternating manner to form a controlled flex region. Referring to FIG. 9, a component 900 includes a more rigid, less flexible member 902 and a more flexible, less rigid member 904 ultrasonically welded to one another in an alternating manner thereby forming a plurality of joints 906 which interconnect the members. The more rigid, less flexible member 902 may be foam, and the more flexible, less rigid member 904 may be a textile. The alternating textiles may allow flexibility in the component 900 in the manner of a gusset.

As shown in FIG. 9, each foam member 902 and each textile 904 may be shaped to provide flexibility or rigidity as desired. In the illustrated example, the foam members 902 and the textile member 904 have varying shapes.

3.1.7 Comfort Pad

A comfort pad may be constructed by an ultrasonic welding process. A patient may overwrap a headgear strap with a comfort pad in order to enhance comfort. A cushioned section of the comfort pad may be situated between the strap and the patient to lessen the pressure of the strap against the patient's skin.

Figures 1, 10:
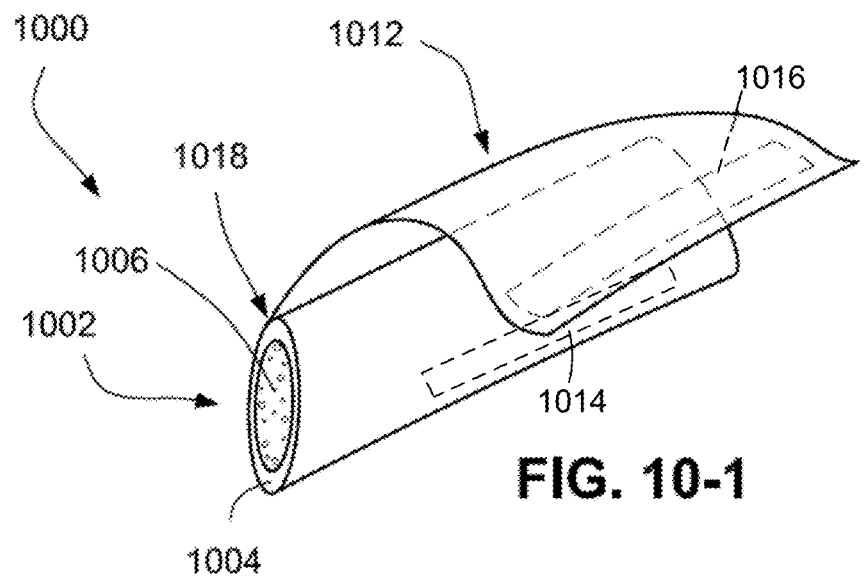
Figures 2, 10:
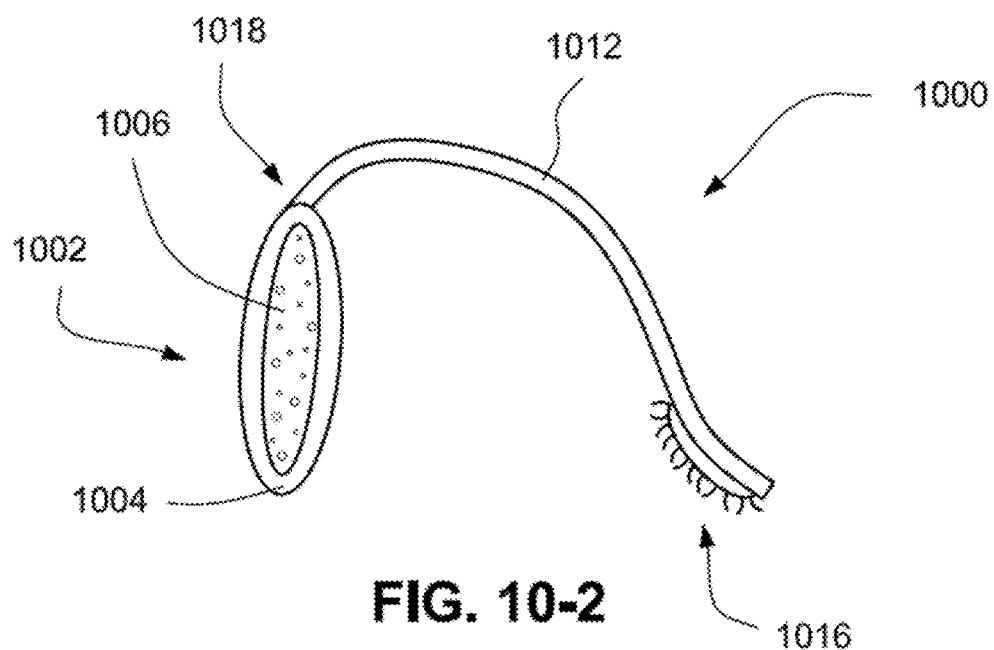

Turning to FIGS. 10-1 and 10-2, a comfort pad 1000 may include a padded section 1002 and a flat section 1012. The padded section may include an outer fabric and an inner cushion layer (e.g., foam). The flat section 1012 is used to overwrap a strap and may include hook material 1016 on an inner surface to cooperate with unbroken loop 1014 on an opposing outer surface. The flat section 1012 may be a fabric and may further be constructed as a low profile section to reduce bulk.

The padded section 1002 may be ultrasonically welded to the flat section 1012 to form a joint 1018 which interconnects the padded section and the flat section. The joint 1018 may be a seamless flush joint that provides a smooth surface which may comfortably contact the patient's skin without causing any or substantial irritation.

Figures 1, 11:
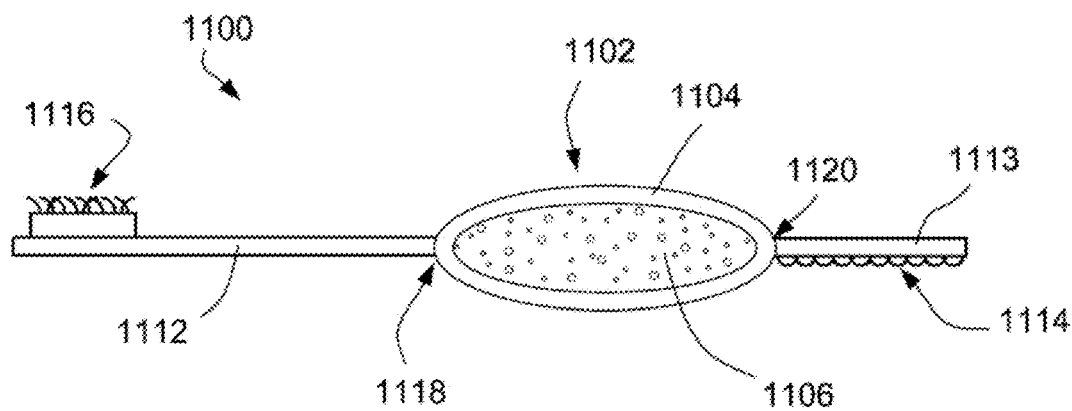
Figures 2, 11:
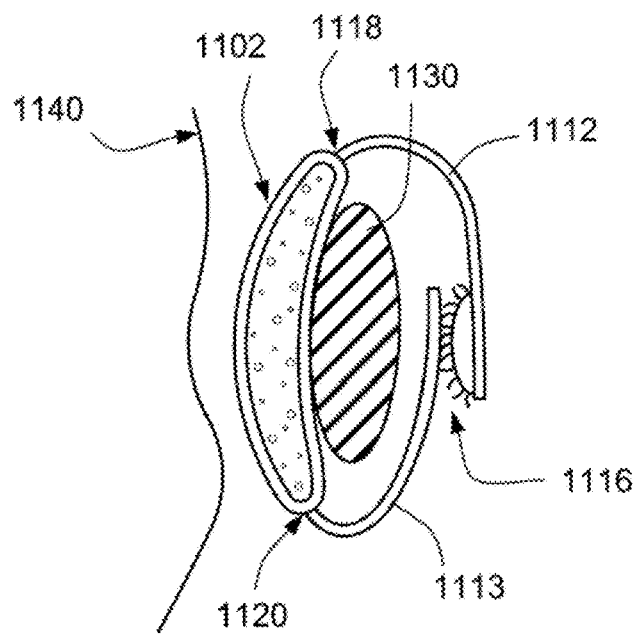
Figures 3, 11:
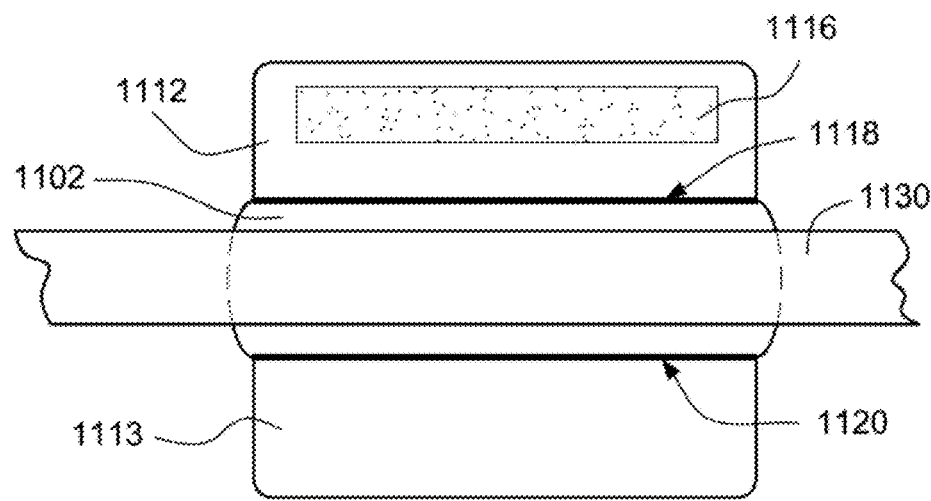

In another example shown in FIGS. 11-1 to 11-3, a comfort pad 1100 may include a first flat section 1112 and a second flat section 1113 on opposite sides of a padded section 1102. This arrangement may enable the comfort pad to more easily wrap around a strap 1130. Similar to the comfort pad 1000, the padded section 1102 may include an outer fabric and an inner cushion layer 1106 (e.g., foam).

Further, the first flat section 1112 may include hook material 1116 on an inner surface to cooperate with unbroken loop 1114 on an outer surface of the section flat section 1113. The first and second flat sections may be formed of fabric and may further be constructed as low profile sections to reduce bulk.

A first joint 1118 interconnects the first flat section 1112 and the padded section 1102, and a second joint 1120 interconnects the second flat section 1113 and the padded section. The joints 1118, 1120 are flush joints that provide smooth surfaces which may comfortably contact the patient's skin 1140 without causing any or substantial irritation.

3.1.8 Mask

Figures 1, 12:
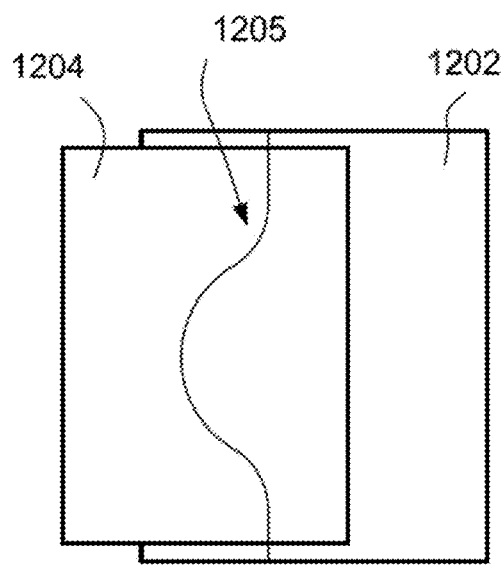
Figures 2, 12:
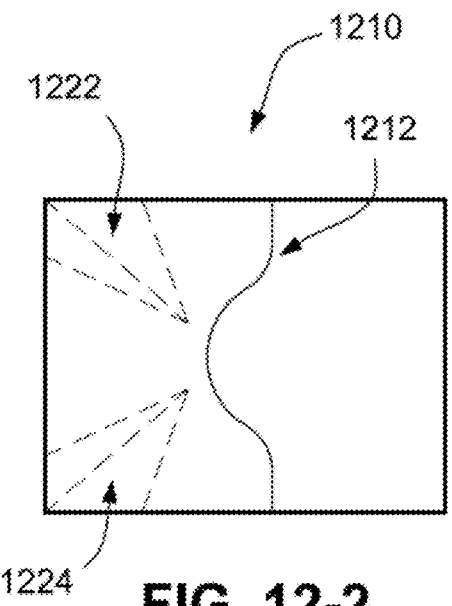
Figures 3, 12:
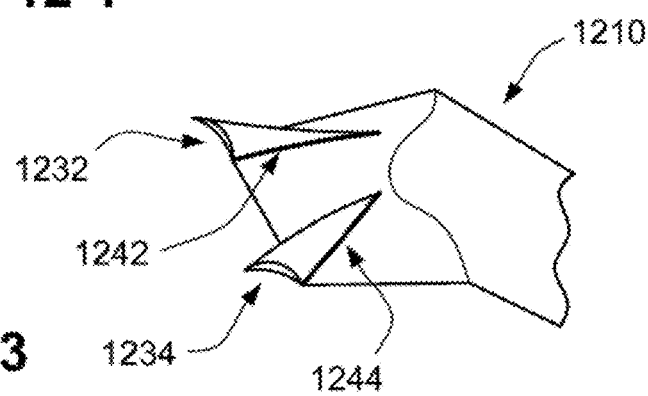
Figures 4, 12:
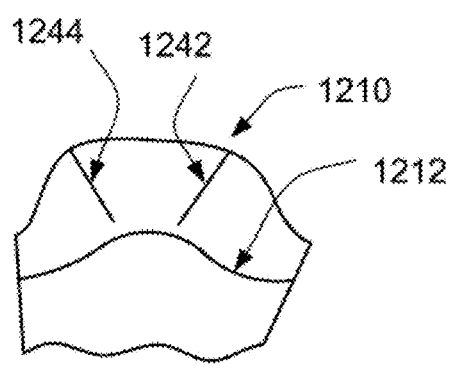
Figures 5, 12:
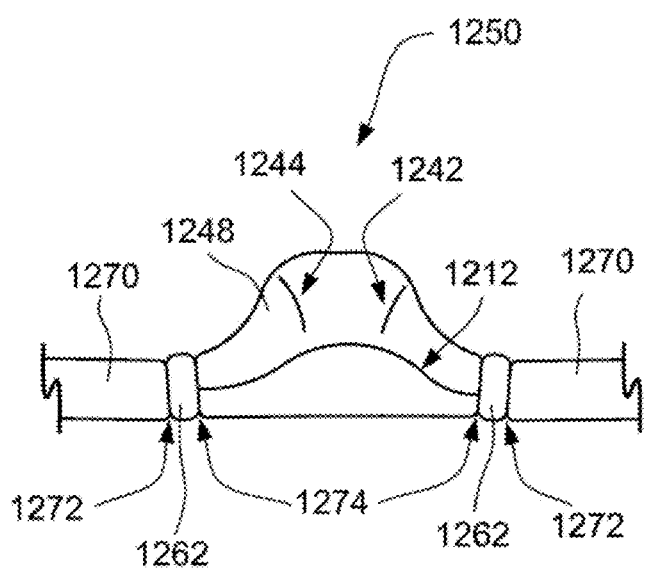

In an example, generally planar components may be formed into a three-dimensional mask by an ultrasonic welding process. It should be noted that the components may have a shape that is not planar. Referring to FIGS. 12-1 and 12-2, a first component 1202 and a second component 1204 may be overlapped in an ultrasonic welding tool and joined along the curved weld line 1205. The ultrasonic welding procedure yields a mask component 1210 which includes a joint 1212 that interconnects the first and second components 1202, 1204. The curved nature of the joint 1212 facilitates a three-dimensional shape when the first and second components 1202, 1204 are pivoted with respect to one another along the joint 1212, as can be seen in FIG. 12-3.

Dart lines 1222, 1224 may be marked on the mask component 1210. The mask component is then later folded along the dart lines to form darts 1232, 1234, which are in turn ultrasonically welded to create a three-dimensional shape in the mask component 1210. The excess fabric in darts 1232 and 1234 may or may not be removed in the process. The ultrasonic weld forms joints 1242, 1244, as shown in FIGS. 12-3 and 12-4.

The three-dimensional shape in the mask component 1210 may form a cavity that supplies pressurized air to a patient. In the illustrated example, the mask component 1210 forms a nasal mask 1248 that seals against a patient's face. Alternatively, the mask 1248 may be a full face mask or other type of mask.

Further, the nasal mask 1248 may be connected to conduits to form a nasal mask assembly 1250. In the illustrated example, cuffs 1262 connect the mask assembly to conduit headgear 1270 (or other gas supply conduits). The conduit headgear 1270 function to at least partially support the mask assembly 1250 on the patient's face while also supplying pressurized air to the patient. It is noted that other conduits and/or headgear may also be used. The conduit headgear 1270 may be ultrasonically welded to the cuffs 1262, thus forming ultrasonic welding joints 1272, and the cuffs 1262 may be ultrasonically welded to the nasal mask 1248 to form joints 1274.

4. Ultrasonic Welding to Create Multiple Component Depth

Components may also be stacked and ultrasonically welded one on top of the other. For example, components may be joined only at their ends such that a space is formed between the components. Alternatively, components may be joined in a manner that does not provide a space.

4.1 Pocket

Figures 1, 13:
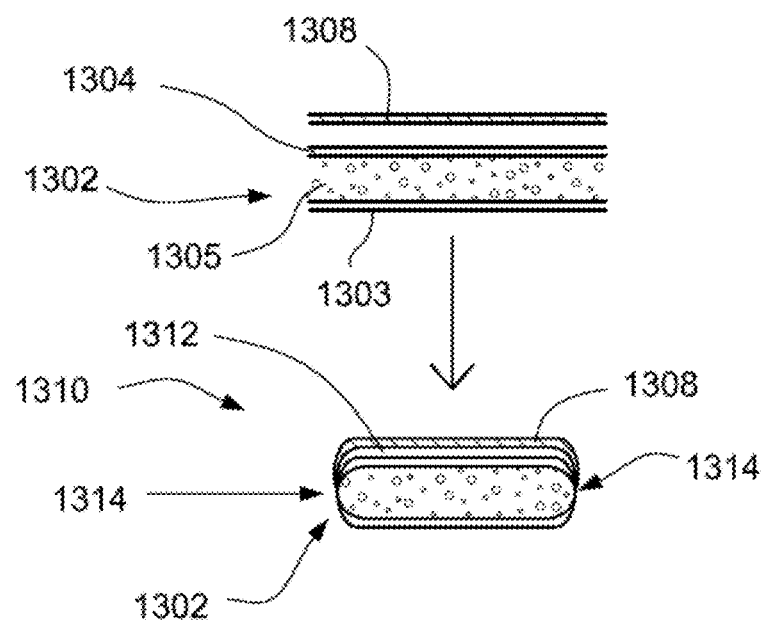
Figures 2, 13:
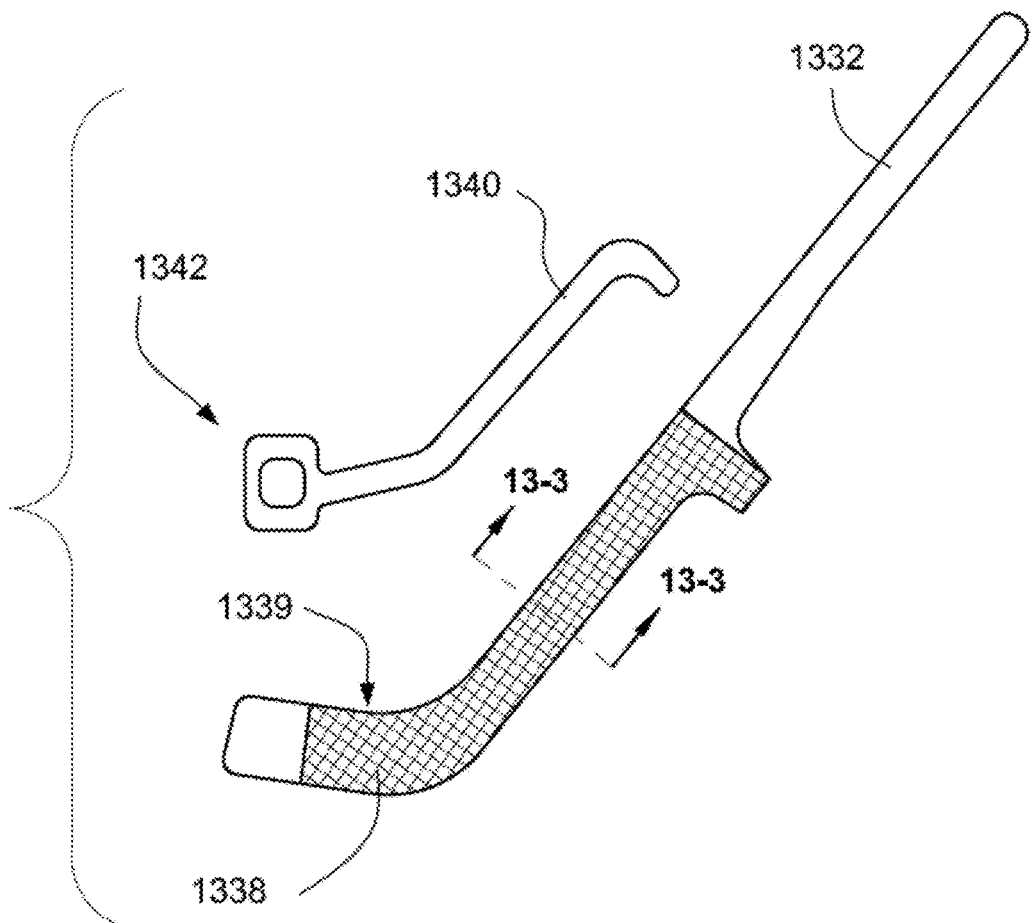
Figures 3, 13:
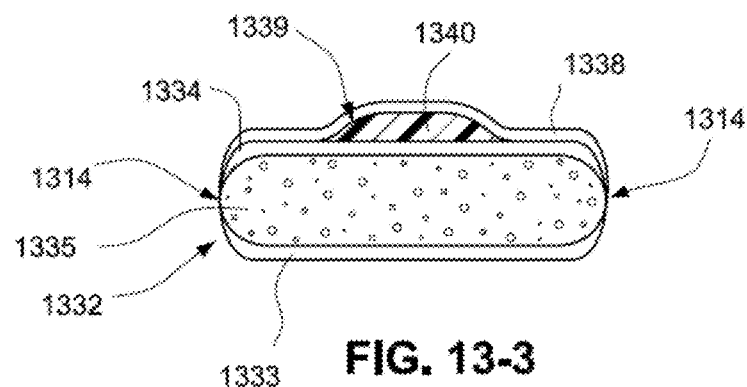
Figures 4, 13:
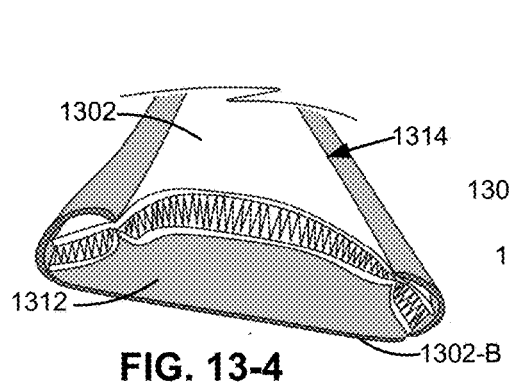
Figures 5, 13:
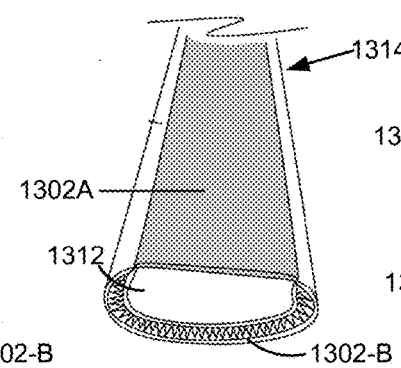
Figures 6, 13:
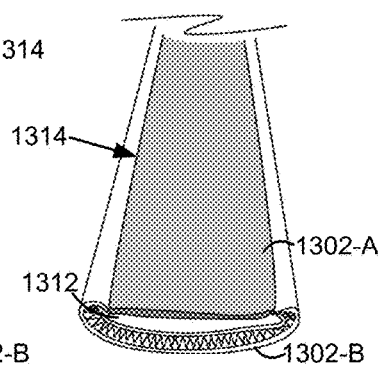

A component 1302 may be ultrasonically welded to a second component, e.g., a pocket fabric 1308 to form a pocket component 1310 having a space or pocket 1312 therebetween, as shown in FIG. 13-1. The component 1302 may include inner 1303 and outer 1304 fabric layers and an inner cushion layer 1305. The cushion layer 1305 may be foam or spacer fabric. The inner and outer layers 1303, 1304 may be formed of a nylon/spandex or elastane combination. In an alternative form, there may be one or two additional layer/s of a heat-fixable TPU (or other thermosensitive polymer) glue sheet welded in between component 1302 and pocket fabric 1308 during the process. This may permit later inserting of a rigidizer component (1342 FIG. 13-2) and affixing a curved or flat rigidizer in place by applying heat and thus melting the TPU glue sheet inside the pockets so as to fuse all of the components together.

The component 1302 may be ultrasonically die cut and welded to round its edges, and the pocket fabric 1308 may be ultrasonically welded to the component 1302 to form joints 1314. The joints 1314 form smooth, flush joints that may enclose the cushioning layer. Since the component 1302 and the pocket fabric 1308 are welded only at their ends, a pocket 1312 is formed between the component and the pocket fabric.

As shown in FIG. 13-2, a pocket 1339 formed between a headgear component 1332 and a pocket fabric 1338 may be used to accommodate a rigidizer 1340. The rigidizer may be formed by injection molding and may further include a clip 1342 for connecting the headgear component to another device such as a mask, held in place by the headgear component. The connection between the headgear component 1332 and the other device may be strengthened by the clip 1342 which is formed of a more rigid material than the headgear component.

In another example, shown in FIG. 13-3, the headgear component 1332 includes inner and outer layers 1333, 1334 and a cushion layer 1335. The headgear component 1332 may be thermoformed with the rigidizer 1340 positioned in the pocket 1339 to fix the rigidizer to the headgear component. The thermoforming process melts a portion of the rigidizer which hardens to secure the rigidizer to the headgear component. Alternatively, the pocket may include an adhesive to secure the rigidizer.

In the example shown in FIG. 13-4, the ultrasonic welding joints 1314 may be located on the outer surface of the component 1302-B away from a patient contacting surface of the component 1302-B. The joints 1314 form smooth, flush joints. Positioning the seams on the outer surface of the component 1302 may enhance comfort by providing a larger continuous surface of the cushioning fabric as a patient contacting surface. It will also provide more cushioning, and may help to relieve facial marking. This example may help create a more rounded edge external profile as shown in FIG. 13-4. A curved profile strap with a rounded edge profile near the patient side is shown in the relaxed condition in FIG. 13-5 and FIG. 13-6 in the compressed condition. For example, the ratio of the width of portion 1302-A to that of the width of 1302-B is less than unity. In FIG. 13-6 the ratio is closer to unity than in FIG. 13-5.

4.1.1 Strap Tidy

Figure 14:
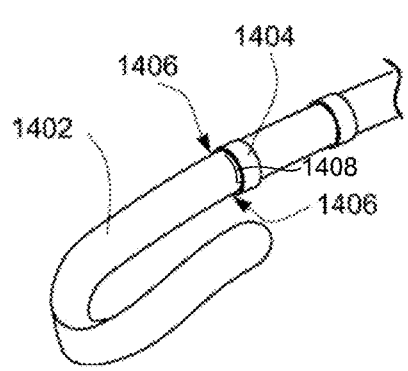
FIG. 14 is a partial perspective view of a component ultrasonically welded to a strap to form a strap tidy according to an example of the disclosed technology.

In another example, a strap of a headgear may be attached to a strap tidy capable of containing the strap as shown in FIG. 14. A pocket 1408 may be formed between a strap 1402 and a piece of fabric or strap tidy 1404 to create a space to hold a loose or free end of the strap 1402. The strap tidy 1404 may be ultrasonically welded to the strap 1402 to form joints 1406, the joints 1406 forming at least one pocket 1408 for accepting the loose or free end of a strap.

4.2 Soft Patient Interface

Figures 1, 15:
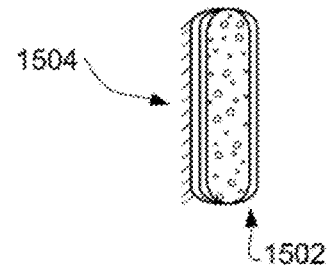

Alternatively, components may be stacked one on top of the other and ultrasonically welded together in a manner that leaves no space therebetween. In an example shown in FIG. 15-1, a headgear component 1502 has inner, outer and cushion layers similar to headgear component 1332. A patient interface component 1504 may be ultrasonically welded to the headgear component 1502 to provide a more comfortable patient interfacing surface. The patient interface component 1504 may be constructed of a soft material, e.g., a soft fabric. The patient interface component 1504 may be welded to the headgear component 1502 at several points or continuously along an inner surface of the patient interface component 1504 and an outer surface of the inner layer of the headgear component 1502. For example, the patient interface component may be a side portion of a mask.

5. Manufacturing

Preferably, the method of manufacturing components may reduce costs by maximizing volume and eliminating material waste. For example, headgear may be designed to have a plurality of common parts such that a plurality of components may have an identical geometry and be located in different sections of the headgear. For instance, headgear 1600 in FIG. 16-1 includes a headgear first component 1602, headgear second component 1604, and headgear third component 1606. Although the portion of headgear 1600 shown in FIG. 16-1 includes seven parts, only three different geometries need to be manufactured to fulfill the parts requirement. Thus, fewer individual component designs are required which may reduce cost.

Figures 1, 16:
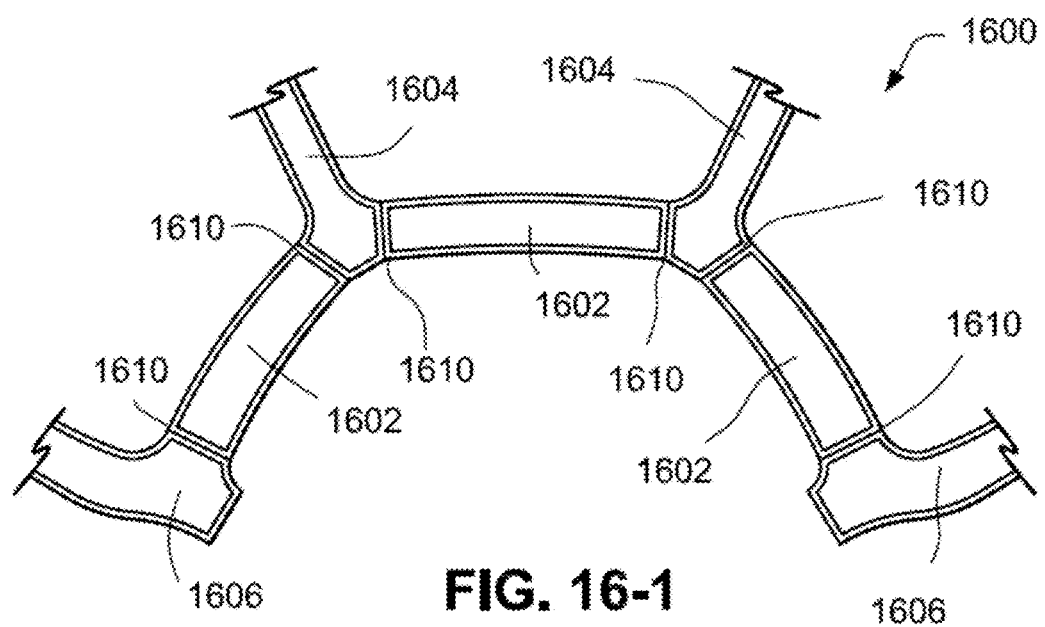
Figures 2, 16:
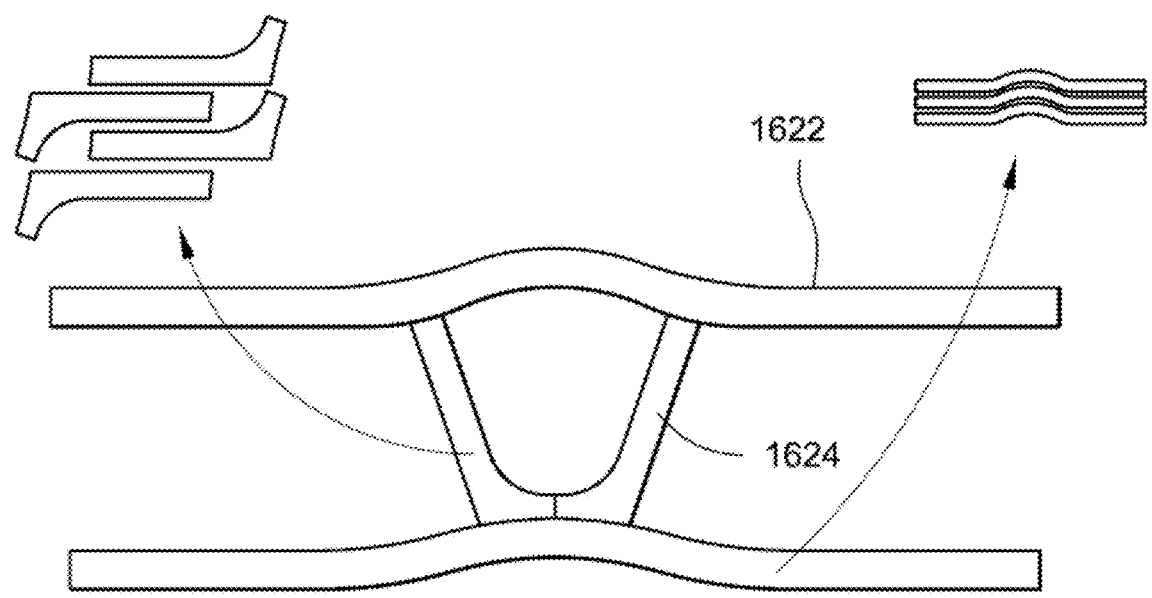

Further, components may be shaped such that they can be nested on the bulk material, such that when they are die cut into individual components, waste is reduced thereby further reducing cost. As an example, headgear fourth component 1622 and headgear fifth component 1624 may be nested to increase yield, as shown in FIG. 16-2. The component parts in FIG. 16-1 may be ultrasonically welded to form joints 1610.

In the foregoing description and in the accompanying drawings, specific terminology, equations and drawing symbols are set forth to provide a thorough understanding of the present technology. In some instances, the terminology and symbols may imply specific details that are not required to practice the technology. For example, although the terms "first" and "second" may be used herein, unless otherwise specified, the language is not intended to provide any specified order but merely to assist in explaining distinct elements of the technology. Moreover, while the technology has been described in connection with several examples, it is to be understood that the technology is not to be limited to the disclosed examples, on the contrary, is intended to cover various modifications and equivalent arrangements included within the spirit and scope of the technology. Also, the various examples described above may be implemented in conjunction with other examples, e.g., one or more aspects of one example may be combined with one or more aspects of another example to realize yet other examples. Further, each independent feature or component of any given assembly may constitute an additional example. In addition, while the technology has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

The invention claimed is:

1. A method of making a comfort pad for use with headgear in holding a respiratory mask in position on a patient's face, comprising:
   ultrasonically welding a padded member to a first substantially flat member thereby forming a first ultrasonic welding joint at a first end of the first substantially flat member, whereby the first ultrasonic welding joint interconnects the padded member and the first substantially flat member,
   wherein the padded member is arranged to provide a cushion between the patient and the headgear, and the first flat member is arranged to overwrap a headgear component of the headgear to position the padded member, and
   wherein the first flat member includes hook material and/or unbroken loop at a second end of the first flat member opposite from the first end.

2. The method of making a comfort pad according to claim 1, wherein the padded member includes a foam layer.

3. The method of making a comfort pad according to claim 1, further comprising ultrasonically welding a second substantially flat member to the padded member thereby forming a second ultrasonic welding joint, the second flat member being joined to the padded member on an opposite side of the padded member than the first flat member.

4. The method of making a comfort pad according to claim 1, wherein the headgear component is a strap of the headgear.

5. The method of making a comfort pad according to claim 1, wherein the first ultrasonic welding joint is a flush joint that provides a smooth surface for contacting the patient's skin.

6. A comfort pad for use with headgear in holding a respiratory mask in position on a patient's face, comprising:
   a padded member and a first substantially flat member, wherein the padded member is ultrasonically welded to the first flat member thereby forming a first ultrasonic welding joint at a first end of the first substantially flat member, whereby the first ultrasonic welding joint configured to interconnect the padded member and the first substantially flat member,
   wherein the padded member is arranged to provide a cushion between the patient and the headgear, and the first flat member is arranged to overwrap a headgear component of the headgear to position the padded member, and
   wherein the first flat member includes hook material and/or unbroken loop at second end of the first flat member opposite from the first end.

7. The comfort pad according to claim 6, wherein the padded member includes a foam layer.

8. The comfort pad according to claim 6, further comprising a second substantially flat member, wherein the second flat member is ultrasonically welded to the padded member thereby forming a second ultrasonic welding joint, the second flat member being joined to the padded member on an opposite side of the padded member than the first flat member.

9. The comfort pad according to claim 6, wherein the headgear component is a strap of the headgear.

10. The comfort pad according to claim 6, wherein the padded member has a single substantially flat member comprising the first substantially flat member.

* * * * *